(12) United States Patent
Sankai

(10) Patent No.: US 7,785,279 B2
(45) Date of Patent: Aug. 31, 2010

(54) WEARABLE ACTION-ASSIST DEVICE, AND METHOD AND PROGRAM FOR CONTROLLING WEARABLE ACTION-ASSIST DEVICE

(75) Inventor: Yoshiyuki Sankai, Tsukuba (JP)

(73) Assignee: University of Tsukuba, Ibaraki (JP)

( * ) Notice: Subject to any disclaimer, the term of this patent is extended or adjusted under 35 U.S.C. 154(b) by 1228 days.

(21) Appl. No.: 10/568,756

(22) PCT Filed: Aug. 13, 2004

(86) PCT No.: PCT/JP2004/011698

§ 371 (c)(1),
(2), (4) Date: Feb. 21, 2006

(87) PCT Pub. No.: WO2005/018525

PCT Pub. Date: Mar. 3, 2005

(65) Prior Publication Data

US 2006/0211956 A1  Sep. 21, 2006

(30) Foreign Application Priority Data

Aug. 21, 2003  (JP)  ............................. 2003-298038
Feb. 20, 2004  (JP)  ............................. 2004-045354

(51) Int. Cl.
*A61H 3/00* (2006.01)
*A61B 5/11* (2006.01)
(52) U.S. Cl. .............................. 601/5; 601/35; 600/595
(58) Field of Classification Search ................ 601/5, 601/23, 33–35, 40; 600/587, 595; 623/25
See application file for complete search history.

(56) References Cited

U.S. PATENT DOCUMENTS 7,537,573 B2 * 5/2009 Horst ............................. 601/5

(Continued)

FOREIGN PATENT DOCUMENTS

EP  1138286 A  10/2001

(Continued)

OTHER PUBLICATIONS

Kuiken et al., "Finite Element Modeling of Electromagnetic Signal Propagation in a Phantom Arm", Dec. 2001, IEEE, vol. 9 No. 4, 346-354.*

(Continued)

*Primary Examiner*—Danton DeMille
(74) *Attorney, Agent, or Firm*—Sughrue Mion, PLLC

(57) ABSTRACT

A wearable action-assist device which assists or executes an action of a wearer by substituting for the wearer is provided with an action-assist tool 2 having an actuator 201 which gives power to the wearer 1, a biosignal sensor 221 which detects a wearer's biosignal, a biosignal processing unit 3 which acquires from a biosignal "a" detected by the biosignal sensor a nerve transfer signal "b" for operating a wearer's muscular line skeletal system, and a myoelectricity signal "c" accompanied with a wearer's muscular line activity, an optional control unit 4 which generates a command signal "d" for causing the actuator 201 to generate power according to the wearer's intention using the nerve transfer signal "b" and the myoelectricity signal "c" acquired by the biosignal processing unit 3, and a driving current generating unit 5 which generates a current according to the nerve transfer signal b and a current according to the myoelectricity signal "c", respectively, based on the command signal "d" generated by the optional control unit 4, and supplies the currents to the actuator 201.

12 Claims, 20 Drawing Sheets

U.S. PATENT DOCUMENTS

2003/0120183 A1* 6/2003 Simmons ................. 600/595

FOREIGN PATENT DOCUMENTS

| JP | 57-125750 A | 8/1982 |
|----|----|----|
| JP | 61-34340 B2 | 8/1986 |
| JP | 2-298479 A | 12/1990 |
| JP | 7-163607 A | 6/1995 |
| JP | 2000-166997 A | 6/2000 |
| JP | 2003-79684 A | 3/2003 |
| JP | 2003-116893 A | 4/2003 |
| WO | 01/13778 A2 | 3/2001 |
| WO | 03/000161 A1 | 1/2003 |

OTHER PUBLICATIONS

Takao Nakai, et al. "Development of Power Assistive Leg for Walking Aid Using EMG and Linux," Second Asian Symposium on Industrial Automation and Robotics, BITECH, Bangkok, Thailand, May 17-18, 2001.

Kota Kasaoka, et al. "Predictive Control Estimating Operator's Intention for Stepping-Up Motion by Exo-Skeleton Type Power Assist System HAL," Proceedings of the 2001 IEEE/RSJ International Conference on Intelligent Robots and Systems, Maui, Hawaii, USA, Oct. 29-Nov. 3, 2001.

Suwoong Lee, et al. "Power Assist Control for Walking Aid by HAL Based on Phase Sequence and EMG," the collection (2001) of academic lecture meeting drafts of the 19$^{th}$ Robotics Society of Japan.

Lee, et al., "Power Assist Control for Leg with HAL-3 Based on EMG and Impedance Adjustment around Knee Joint", 20th Japan Robotics Meeting Papers (CD-ROM), Oct. 12, 2002, 1F34, Abstract.

Jacob Buus Andersen et al., "An Actuator System for Investigating Electrophysiological and Biomechanical Features Around the Human Ankle Joint During Gait", IEEE Transaction on Rehabilitation Engineering, Dec. 1, 1995, pp. 299-306, vol. 3 No. 4, IEEE Inc., New York, USA.

* cited by examiner

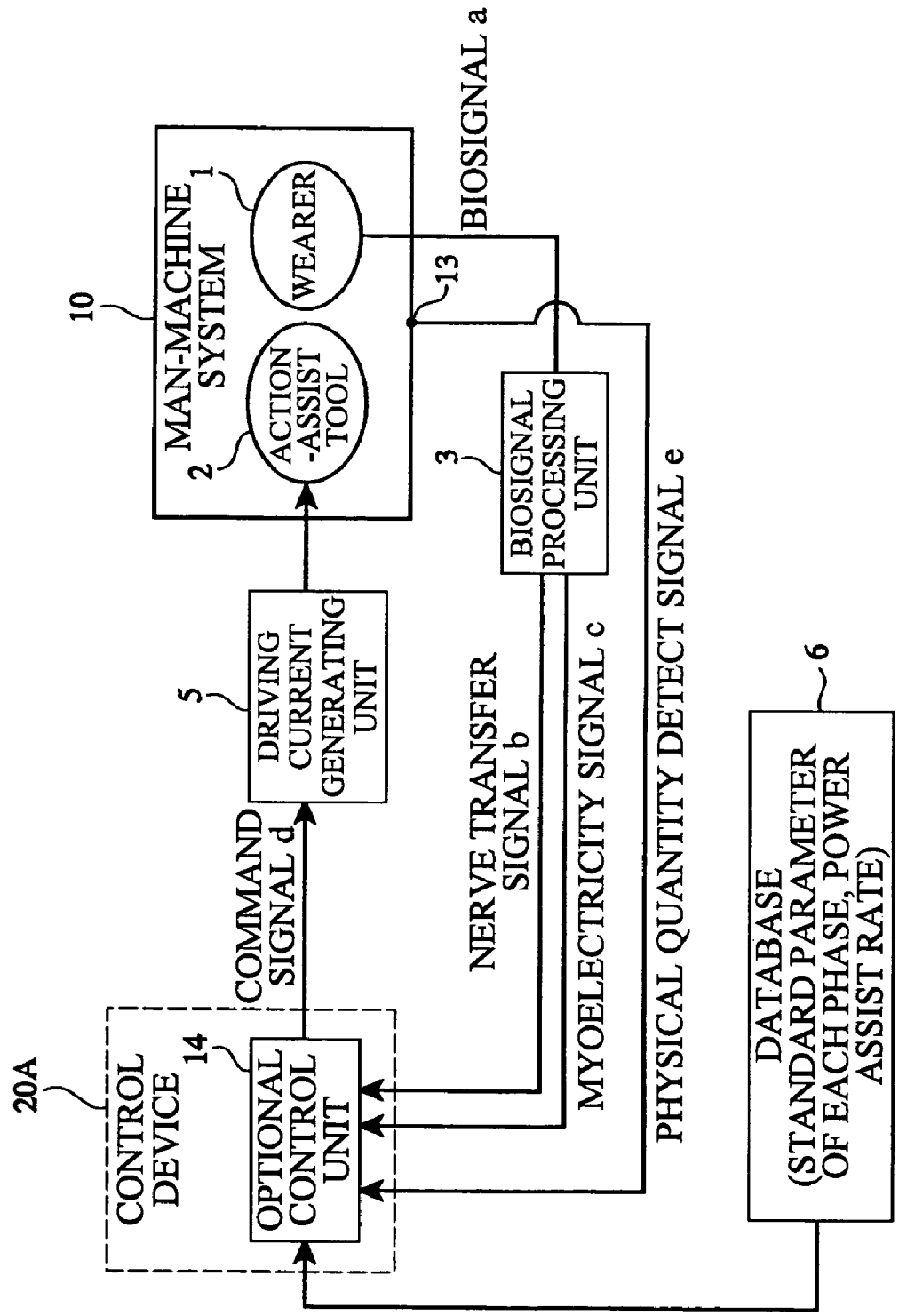

FIG.11
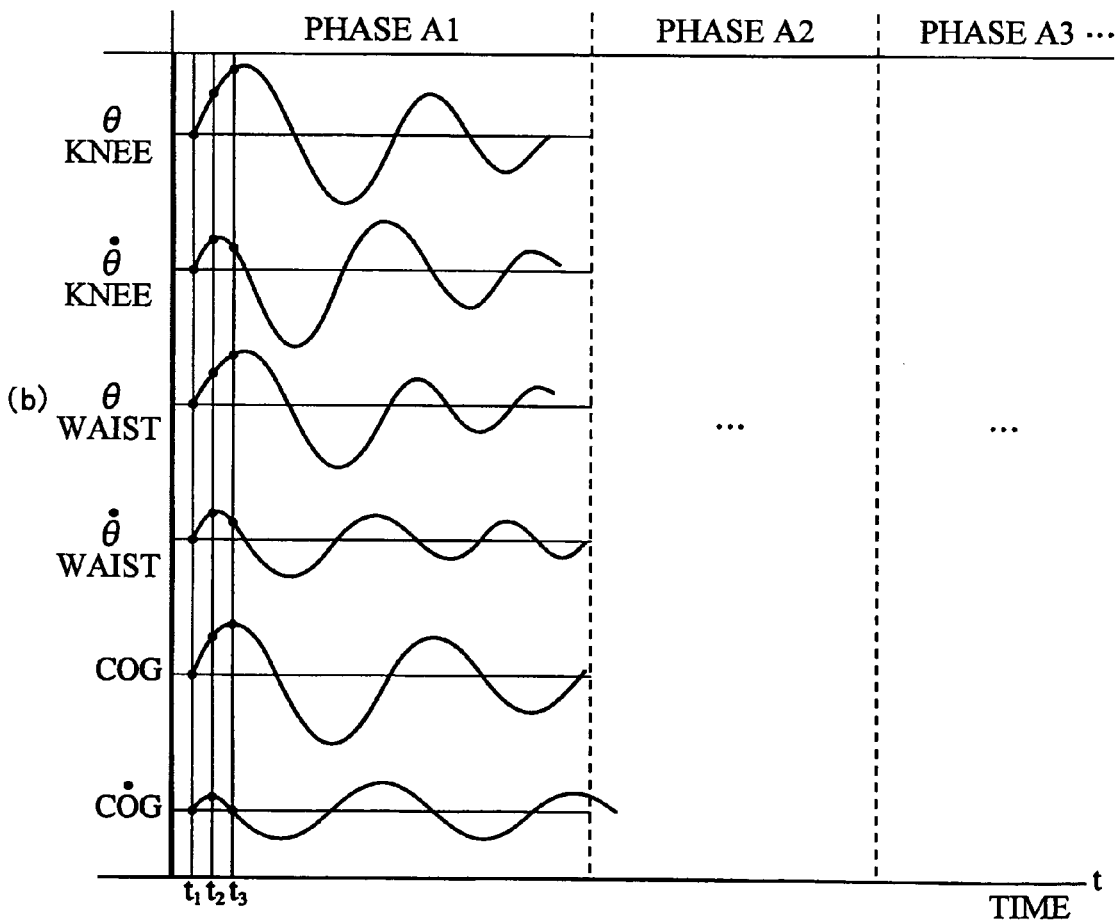
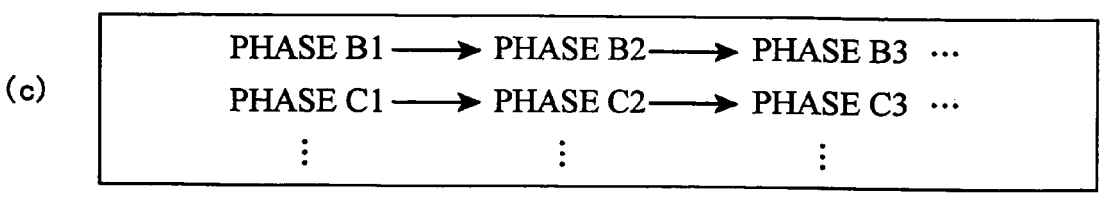

WEARABLE ACTION-ASSIST DEVICE, AND METHOD AND PROGRAM FOR CONTROLLING WEARABLE ACTION-ASSIST DEVICE

This application claims priority from PCT Application No. PCT/JP2004/011698 filed Aug. 13, 2004, from Japanese Application No. 2003-298038 filed Aug. 21, 2003, and from Japanese Patent Application No. 2004-045354 filed Feb. 20, 2004, which applications are incorporated herein by reference.

TECHNICAL FIELD

The present invention relates to a wearable action-assist device and a method and program for controlling a wearable action-assist device which assists or executes an action of the wearer by substituting for the wearer. More particularly, the present invention relates to a wearable action-assist device and a method and program for controlling a wearable action-assist device which can suppress the sense of incongruity given to the wearer when controlling the wearable action-assist device.

BACKGROUND ART

In many cases, it is difficult for physically handicapped or elderly people to perform an operation which can be performed easily by a healthy person.

Until today, various action-assist devices have been developed and put in practical use for such people. The action-assist devices may include a wheelchair or a care bed on which the user rides and operates a switch to drive an actuator, such as a motor, so as to assist the insufficient power. The action-assist devices may also include a wearable device which is worn by the human being and assists power needed for operation of the device based on the wearer's intention.

What is called a wearable action-assist device that can be worn by the wearer can generate a required power at any time based on the wearer's intention and a care worker is not needed. Thus, the wearable action-assist device is very useful for rehabilitation of injured or sick people and care of physically disabled persons, elderly people, etc. and its utilization is expected to grow.

There has been proposed such a wearable action-assist device in which a myoelectricity signal accompanied with a wearer's muscular line activity is detected, and an actuator is driven based on the detection result. In this wearable action-assist device, the actuator is controlled optionally according to the wearer's intention.

See the non-patent literature 1 (Takao Nakai, Suwoong Lee, Hiroaki Kawamoto and Yoshiyuki Sankai, "Development of Power Assistive Leg for Walking Aid using EMG and Linux", Second Asian Symposium on Industrial Automation and Robotics, BITECH, Bangkok, Thailand, May 17-18, 2001).

In the meantime there is a problem in a wearable action-assist device in that, if the timing which gives the wearer the power for assistance does not harmonize with a motion of the wearer, the wearer's action becomes awkward and a sense of incongruity is given to the wearer.

It is known that, in order to harmonize the timing of power application with the motion of the wearer, it is necessary to make the timing of power application earlier than the motion of the wearer by a minute time.

However, in the wearable action-assist device of the non-patent literature 1, the processing for causing an actuator to generate power is started after the myoelectricity signal from the wearer is detected, and there is a possibility that the timing of power application later than the motion of the wearer may give the wearer a remarkable sense of incongruity.

To avoid the problem, a conventional device is proposed in which a drive control of an actuator is carried out in the following manner. The human being's action is classified into a plurality of patterns (tasks) and each task is divided into a plurality of predetermined minimum action units (phases), and a predetermined amount of current is supplied to the actuator for every phase.

See the non-patent literature 2 ("Predictive Control Estimating Operator's Intention for Stepping-up Motion by Exo-Skeleton Type Power Assist System HAL", Proceedings of the 2001 IEEE/RSJ and International Conference on Intelligent Robots and Systems, Maui, Hi., Oct. 29-Nov. 3, 2001, pp. 1578-1583), and the non-patent literature 3 (Hideo Lee and Yoshiyuki Sankai, "Power Assist Control of Walking Aid by HAL Based on Phase Sequence and EMG", the collection (2001) of academic lecture meeting drafts of the 19th Robotics Society of Japan).

In the wearable action-assist devices of the non-patent literatures 2 and 3, a phase of a wearer's task is estimated based on a physical quantity, such as a joint angle, which is detected from the wearer, and an actuator is controlled according to the estimated phase (autonomous control), in order to reduce the sense of incongruity accompanied with the delay of the timing of power application.

DISCLOSURE OF THE INVENTION

Problem to be Solved by the Invention

However, the control systems of the wearable action-assist devices of the above-mentioned non-patent literatures 2 and 3 are provided to depend on the autonomous control, and if an unexpected change to the action, such as a stumble, occurs, it is difficult to smoothly perform switching to a phase of a corresponding task. And there is a possibility that a remarkable sense of incongruity may be given to the wearer.

Accordingly, an object of the present invention is to provide a wearable action-assist device and a method and program for controlling a wearable action-assist device in which the above-mentioned problems are eliminated and the sense of incongruity given to the wearer can be suppressed as much as possible.

Means for Solving the Problem

In order to achieve the above-mentioned object, the present invention provides a wearable action-assist device which assists or executes an action of a wearer by substituting for the wearer, the wearable action-assist device comprising: an action-assist tool having an actuator which gives power to the wearer; a biosignal sensor detecting a wearer's biosignal; a biosignal processing unit acquiring, from the biosignal detected by the biosignal sensor, a nerve transfer signal for operating a wearer's muscular line skeletal system, and a myoelectricity signal accompanied with a wearer's muscular line activity; an optional control unit generating a command signal for causing the actuator to generate power according to a wearer's intention by using the nerve transfer signal and the myoelectricity signal which are acquired by the biosignal processing unit; and a driving current generating unit generating a current according to the nerve transfer signal and a current according to the myoelectricity signal, respectively, based on the command signal generated by the optional control unit, to supply the respective currents to the actuator.

In order to achieve the above-mentioned object, the present invention provides a method of controlling a wearable action-assist device which assists or executes an action of a wearer by substituting for the wearer, wherein an action-assist tool having an actuator which gives power to the wearer is attached to the wearer, the method comprising the steps of: detecting a wearer's biosignal; acquiring, from the detected biosignal, a nerve transfer signal for operating a wearer's muscular line skeletal system and a myoelectricity signal accompanied with a wearer's muscular line activity; generating an optional command signal for causing the actuator to generate power according to a wearer's intention by using the nerve transfer signal and the myoelectricity signal which are acquired; and generating a current according to the nerve transfer signal and a current according to the myoelectricity signal, respectively, based on the generated optional command signal, to supply the respective currents to the actuator.

In order to achieve the above-mentioned object, the present invention provides a program for causing a computer to execute a method of controlling a wearable action-assist device which assists or executes an action of a wearer by substituting for the wearer, wherein an action-assist tool having an actuator which gives power to the wearer is attached to the wearer, the method comprising the steps of: detecting a wearer's biosignal; acquiring, from the detected biosignal, a nerve transfer signal for operating a wearer's muscular line skeletal system and a myoelectricity signal accompanied with a wearer's muscular line activity; generating an optional command signal for causing the actuator to generate power according to a wearer's intention by using the nerve transfer signal and the myoelectricity signal which are acquired; and generating a current according to the nerve transfer signal and a current according to the myoelectricity signal, respectively, based on the generated optional command signal, to supply the respective currents to the actuator.

The above-mentioned the wearable action-assist device may be configured so that the wearable action-assist device comprises a physical quantity sensor which detects a physical quantity related to the action of the wearer.

The above-mentioned wearable action-assist device may be configured so that the biosignal processing unit comprises: a unit which amplifies the biosignal; a first filter which extracts the nerve transfer signal from the biosignal; and a second filter which extracts the myoelectricity signal from the biosignal.

The above-mentioned wearable action-assist device may be configured so that the driving current generating unit supplies to the actuator a total current of a pulse current which is generated according to the nerve transfer signal and a current which is generated so as to be substantially proportional to the myoelectricity signal, and causes operation of the actuator to start by supplying the pulse current.

The above-mentioned wearable action-assist device may be configured so that the driving current generating unit generates, when starting the supply of current to the actuator, the pulse current or the total current such that the pulse current or the total current is larger than a lower limit of current that is capable of driving the actuator.

The above-mentioned wearable action-assist device may be configured so that the wearable action-assist device comprises a database in which a given correspondence relation between each of respective standard parameters of a series of minimum action units (phases) which constitute a wearer's action pattern classified as a task, and a power application rate (power assist rate) of the actuator is stored, and the optional control unit estimates a phase of a task which the wearer intends to perform, by comparing the physical quantity detected by the physical quantity sensor with a standard parameter stored in the database, the optional control unit determining a power assist rate according to the estimated phase based on the correspondence relation, and generating a command signal for causing the actuator to generate a power according to the power assist rate.

The above-mentioned wearable action-assist device may be configured so that, when the wearer operates by reflexes, the driving current generating unit supplies a current for driving the actuator in an opposite direction of the operation concerned for a predetermined time, and, after the predetermined time, the driving current generating unit supplies a current for driving the actuator in a direction towards the operation.

The above-mentioned method of controlling the wearable action-assist device may be configured so that a total current of a pulse current which is generated according to the nerve transfer signal and a current which is generated so as to be substantially proportional to the myoelectricity signal is supplied to the actuator, and operation of the actuator is caused to start by supplying the pulse current.

The above-mentioned method of controlling the wearable action-assist device may be configured so that, when starting the supply of current to the actuator, the pulse current or the total current is generated such that the pulse current or the total current is larger than a lower limit of current that is capable of driving the actuator.

The above-mentioned method of controlling the wearable action-assist device may be configured so that the method further comprises the steps of: detecting a physical quantity related to the action of the wearer; estimating a phase of a task which the wearer intends to perform, by comparing the physical quantity with each of respective standard parameters of a series of minimum action units (phases) which constitute a wearer's action pattern classified as a task; determining a power assist rate according to the estimated phase based on the correspondence relation; and generating a command signal for causing the actuator to generate a power according to the power assist rate.

The above-mentioned method of controlling the wearable action-assist device may be configured so that, when the wearer operates by reflexes, a current for driving the actuator in an opposite direction of the operation concerned for a predetermined time is supplied, and, after the predetermined time, a current for driving the actuator in a direction towards the operation is supplied.

Moreover, in order to achieve the above-mentioned object, the present invention provides a wearable action-assist device which assists or executes an action of a wearer by substituting for the wearer, the wearable action-assist device comprising: an action-assist tool having an actuator which gives power to the wearer; a biosignal sensor detecting a wearer's biosignal; a physical quantity sensor detecting a physical quantity related to the action of the wearer; an optional control unit generating a command signal for causing the actuator to generate power according to a wearer's intention, by using the biosignal detected by the biosignal sensor, a database storing respective standard parameters of a series of minimum action units (phases) which constitute a wearer's action pattern classified as a task; an autonomous control unit estimating a phase of the wearer's task by comparing the physical quantity detected by the physical quantity sensor with a standard parameter stored in the database, and generating a command signal for causing the actuator to generate power according to the estimated phase; a signal combining unit combining the command signal from the optional control unit and the command signal from the autonomous control unit; and a driving current generating unit generating a total current according to a total command signal from the signal combining unit, to supply the total current to the actuator.

Moreover, in order to achieve the above-mentioned object, the present invention provides a method of controlling a wearable action-assist device which assists or executes an action of a wearer by substituting for the wearer, wherein an action-assist tool having an actuator which gives power to the wearer is attached to the wearer, the method comprising the steps of: detecting a wearer's biosignal; acquiring, from the detected biosignal, a nerve transfer signal for operating a wearer's muscular line skeletal system and a myoelectricity signal accompanied with a wearer's muscular line activity; generating an optional command signal for causing the actuator to generate power according to a wearer's intention by using the nerve transfer signal and the myoelectricity signal which are acquired; and generating a current according to the nerve transfer signal and a current according to the myoelectricity signal, respectively, based on the generated optional command signal, to supply the respective currents to the actuator.

Moreover, in order to achieve a program for causing a computer to execute a method of controlling a wearable action-assist device which assists or executes an action of a wearer by substituting for the wearer, wherein an action-assist tool having an actuator which gives power to the wearer is attached to the wearer, the method comprising the steps of: detecting a wearer's biosignal; acquiring, from the detected biosignal, a nerve transfer signal for operating a wearer's muscular line skeletal system and a myoelectricity signal accompanied with a wearer's muscular line activity; generating an optional command signal for causing the actuator to generate power according to a wearer's intention by using the nerve transfer signal and the myoelectricity signal which are acquired; and generating a current according to the nerve transfer signal and a current according to the myoelectricity signal, respectively, based on the generated optional command signal, to supply the respective currents to the actuator.

The above-mentioned the wearable action-assist device may be configured so that a plurality of hybrid ratios of the command signal from the optional control unit and the command signal from the autonomous control unit which have a given correspondence relation with the respective standard parameters of the series of phases are stored in the database, and the signal combining unit combines the command signal from the optional control unit and the command signal from the autonomous control unit so as to meet a hybrid ratio which is determined based on the correspondence relation according to the phase estimated by the autonomous control unit.

The above-mentioned wearable action-assist device may be configured so that the wearable action-assist device comprises a biosignal processing unit which acquires, from the biosignal detected by the biosignal sensor, a nerve transfer signal for operating a wearer's muscular line skeletal system and a myoelectricity signal accompanied with a wearer's muscular line activity, and the driving current generating unit causes operation of the actuator to start by supplying a pulse current which is generated according to the nerve transfer signal acquired by the biosignal processing unit.

The above-mentioned wearable action-assist device may be configured so that the driving current generating unit generates the pulse current or the total current so that it may become larger than a lower limit of current which can drive the actuator when starting supply of current to the actuator.

The above-mentioned wearable action-assist device may be configured so that a plurality of power application rates (power assist rates) of the actuator, which have a given correspondence relation with the respective standard parameters of the series of phases, are stored in the database, and the signal combining unit determines a power assist rate according to the phase of the task estimated by the autonomous control unit based on the correspondence relation, and the optional control unit, and combines the command signal from the optional control unit and the command signal from the autonomous control unit so as to meet the determined power assist rate.

The above-mentioned wearable action-assist device may be configured so that, when the wearer operates by reflexes, the driving current generating unit supplies a current for driving the actuator in an opposite direction of the operation concerned for a predetermined time, and, after the predetermined time, the driving current generating unit supplies a current for driving the actuator in a direction towards the operation.

The above-mentioned method of controlling the wearable action-assist device may be configured so that a plurality of hybrid ratios of the optional command signal and the autonomous command signal which have a given correspondence relation with the respective standard parameters of the series of phases are predetermined, a hybrid ratio is determined based on the correspondence relation according to the estimated phase, and the optional command signal and the autonomous command signal are combined so as to meet the determined hybrid ratio.

The above-mentioned method of controlling the wearable action-assist device may be configured so that, when starting supplying of a current to the actuator, the pulse current or the total current is generated so that it may become larger than a lower limit of a current which can drive the actuator.

The above-mentioned method of controlling the wearable action-assist device may be configured so that a plurality of power application rates (power assist rates) of the actuator, which have a given correspondence relation with the respective standard parameters of the series of phases, are stored, and a power assist rate is determined according to the estimated phase of the task based on the correspondence relation, and the optional command signal and the autonomous command signal are combined so as to meet the determined power assist rate.

The above-mentioned method of controlling the wearable action-assist device may be configured so that, when the wearer operates by reflexes, a driving current for driving the actuator in an opposite direction of the operation concerned is supplied for a predetermined time, and after the predetermined time, a driving current for driving the actuator in a direction towards the operation is supplied.

Effects of the Invention

According to this invention, the myoelectricity signal is acquired from the biosignal, and the nerve transfer signal which precedes with it or is located in the head part of the myoelectricity signal is acquired. The acquired nerve transfer signal is used as a signal (trigger signal) for stating the driving of the actuator, the actuator can be operated promptly when the current supply to the actuator is started. For this reason, it is possible to provide a smooth, comfortable operation which does not feel the delay at the time of starting of the wearable action-assist device.

According to this invention, the optional command signal for causing the actuator to generate the power according to the wearer's intention, and the autonomous command signal for causing the actuator to generate the power according to the phase of the task estimated by the comparison of the detected physical quantity and the standard parameter stored in the database are combined. The starting of the actuator can be carried out quickly, and the optional operation can be performed smoothly and comfortably.

According to this invention, by controlling the hybrid ratio of the optional command signal and the autonomous command signal, no delay of the starting of power assistance arises and the optimal assistance to the wearer's muscular power can be performed. If the hybrid ratio stored in the database is read out for every phase, the hybrid ratio can be changed automatically. Thereby, a more smooth action can be carried out by using the hybrid ratio suitable for each operation.

According to this invention, the total current of the pulse current generated according to the nerve transfer signal and the current generated so that it is substantially proportional to the myoelectricity signal is supplied to the actuator, and the operation of the actuator is started by the supply of the pulse current. Therefore, the delay of the start of the driving of the actuator can be prevented.

If the pulse current or the total current is less than the current that can start the driving of the actuator, the pulse current or the total current is amplified so that it is above the actuator drive starting current. It is possible to make the amplified pulse current correctly respond to the nerve transfer signal when the driving of the actuator is started.

According to this invention, when the wearer operates by reflexes, the current for driving the actuator in an opposite direction of the operation concerned for a predetermined time is supplied, and, after the predetermined time, the current for driving the actuator in a direction towards the operation is supplied. Thus, the wearer's operation can be made smooth using the wearer's reflexes.

According to this invention, the actuator is caused to generate the power which meets the power assist rate according to the phase of the task estimated by comparing the physical quantity with the standard parameter. It is possible to give the optimal power to another wearer of a different physical strength, and the power assistance to the wearer can be carried out.

When the wearable action-assist device of this invention having the above features is used, wearers having no sufficient muscular power, like physically handicapped persons or elderly people, are allowed to smoothly and comfortably perform a physical action which would be difficult to perform without the action-assist device. As for people who must wear a heavy protector in order to perform dangerous work, like the processing of an explosive, the wearable action-assist device of this invention can be used to work lightly as if the heavy protector was not worn.

BRIEF DESCRIPTION OF THE DRAWINGS

FIG. 7A shows the example of the driving current in which the pulse current and the driving current are not superimposed and the pulse current is less than the lower-limit drive start current It, and FIG. 7B shows the example of the driving current in which the pulse current in the state of FIG. 7A is amplified so that it may be larger than the lower-limit drive start current It.

FIG. 8A shows the example of the driving current in which the pulse current and the driving current are superimposed and the total current (equivalent to the current at the rising edge) is less than the lower-limit drive start current It, and FIG. 8B shows the example of the driving current in which the total current in the state of FIG. 8A is amplified so that it may be larger than the lower-limit drive start current It.

FIG. 9 is a block diagram showing an example of the composition which controls a power assist rate in the wearable action-assist device of the first embodiment.

FIG. 11 is a diagram for explaining the process which estimates the phase of the task which the wearer 1 is trying to perform, by comparing a physical quantity with a standard parameter. FIG. 11 (a) shows a database of phases of each task for every action of the wearer, FIG. 11 (b) shows the changes of each of the knee rotation angle θ and its angular velocity θ', the waist rotation angle θ and its angular velocity θ', and the centroid position COG and its moving speed COG', and FIG. 11 (c) shows the state where all the phases (A1, A2, A3 . . . , B1, B2, B3 . . . , C1, C2, C3 . . . ) are taken out in a matrix formation.

FIG. 19 (a) shows the change of the knee rotation angle θ, FIG. 19 (b) shows the change of the biosignal which is amplified, and FIG. 19 (c) shows the change of the torque of the knee actuator.

FIG. 20 (a) shows the change of the knee rotation angle θ, FIG. 20 (b) shows the change of the biosignal which is amplified, and FIG. 20 (*c*) shows the change of the torque of the knee actuator.

FIG. 21 (*a*) shows a phase number, FIG. 21 (*b*) shows the change of the knee rotation angle θ, FIG. 21 (*c*) shows the change of the knee torque by the autonomous control, FIG. 21 (*d*) shows the change of the knee torque by the optional control, and FIG. 21 (*e*) shows the change of the knee torque by the hybrid control (autonomous control+optional control).

FIG. 22 (*a*) shows a phase number, FIG. 22 (*b*) shows the change of the knee rotation angle θ, FIG. 22 (*c*) shows the change of the knee torque by the autonomous control, FIG. 22 (*d*) shows the change of the knee torque by the optional control, and FIG. 22 (*e*) shows the change of the knee torque by the hybrid control (autonomous control+optional control).

Figure 1:
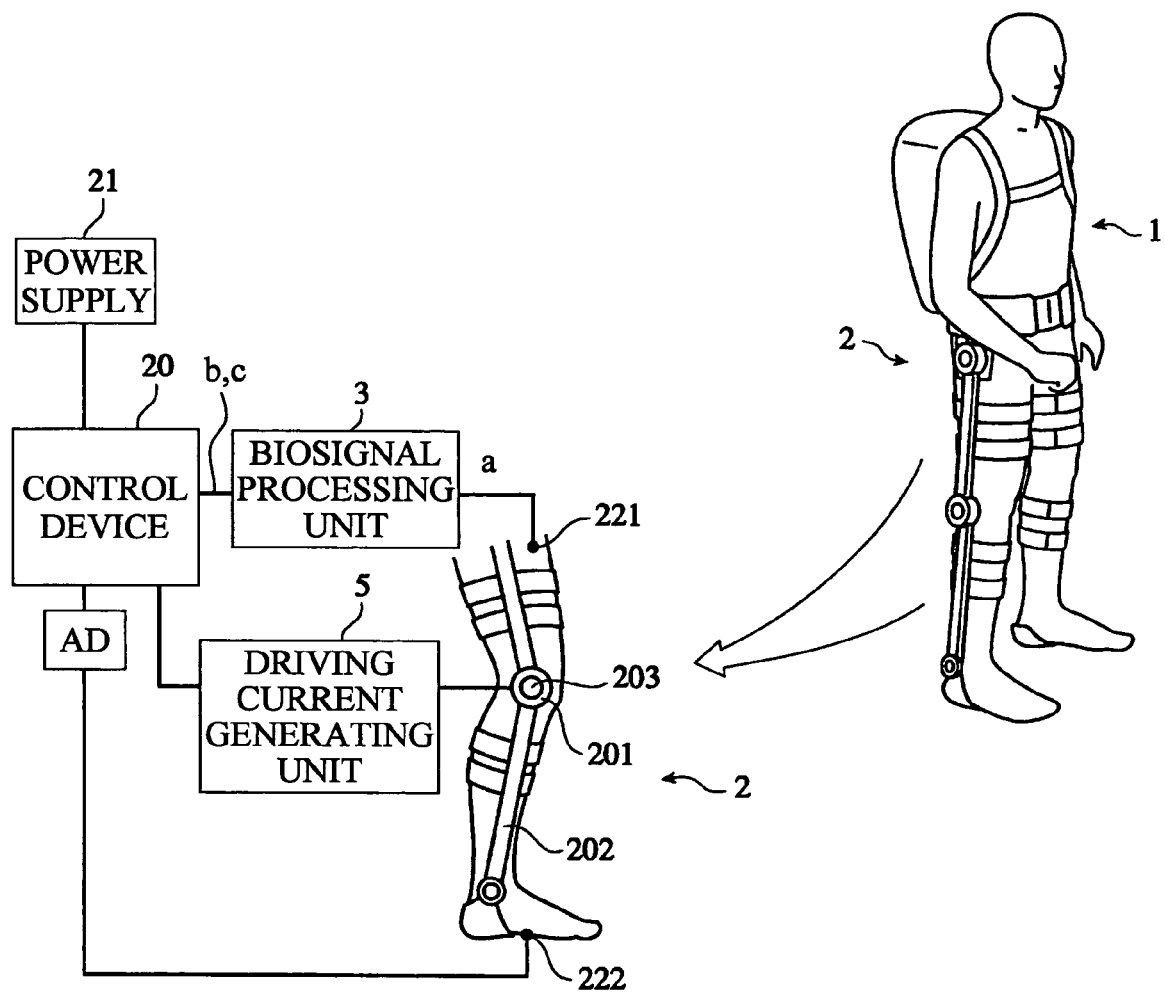
FIG. 1 is a diagram showing the composition of the whole wearable action-assist device.

DESCRIPTION OF REFERENCE NUMERALS 1 man (wearer)
2 action-assist tool
3 biosignal processing unit
4, 14, 24 optional control unit
5 driving current generating unit
6 database
7, 17 autonomous control unit
8 command signal combining unit
10 man-machine system
13 physical quantity sensor
20, 20A, 20B, 20C control device
21 power supply
201 actuator
202 arm
203 joint
221 biosignal sensor
222 barycenter sensor

BEST MODE FOR CARRYING OUT THE INVENTION

A description will now be given of an embodiment of the invention with reference to the accompanying drawings.

[1] First Embodiment (A) Composition of Wearable Action-Assist Device

The wearable action-assist device of the first embodiment comprises an action-assist tool having an actuator, a biosignal sensor which detects a wearer's biosignal, a biosignal processing unit which acquires a nerve transfer signal and a myoelectricity signal from the biosignal, an optional control unit which generates a command signal for causing the actuator to generate power according to a wearer's intention by using the nerve transfer signal and the myoelectricity signal, and a driving current generating unit which generates a current according to the nerve transfer signal and a current according to the myoelectricity signal, respectively, based on the command signal from the optional control unit, to supply the respective currents to the actuator.

When causing the actuator to generate the power that meets the power assist rate according to the phase of the task which the wearer is trying to perform, this wearable action-assist device is provided with a physical quantity sensor which detects a physical quantity related to the action of the wearer.

(1) Drive System

FIG. 1 shows the composition of the whole wearable action-assist device as the drive system (hard system). This wearable action-assist device includes an action-assist tool 2 (the illustration of the other leg is omitted) which is attached to the lower half of the body of the man (called the wearer) 1, a biosignal sensor 221 which detects a biosignal a from the lower half of the body (for example, the thigh), a barycenter sensor 222 which is attached to the sole of the wearer and detects a wearer's center of gravity, a biosignal processing unit 3 which acquires a nerve transfer signal b and a myoelectricity signal c from the biosignal detected by the biosignal sensor 221, a control device 20 which controls the drive of the actuator 201 of the action-assist tool 2 based on the nerve transfer signal b and the myoelectricity signal c, and a power supply (a battery, an external power supply) 21 for supplying electric power to the control device 20 and the actuator 201.

Figure 2:
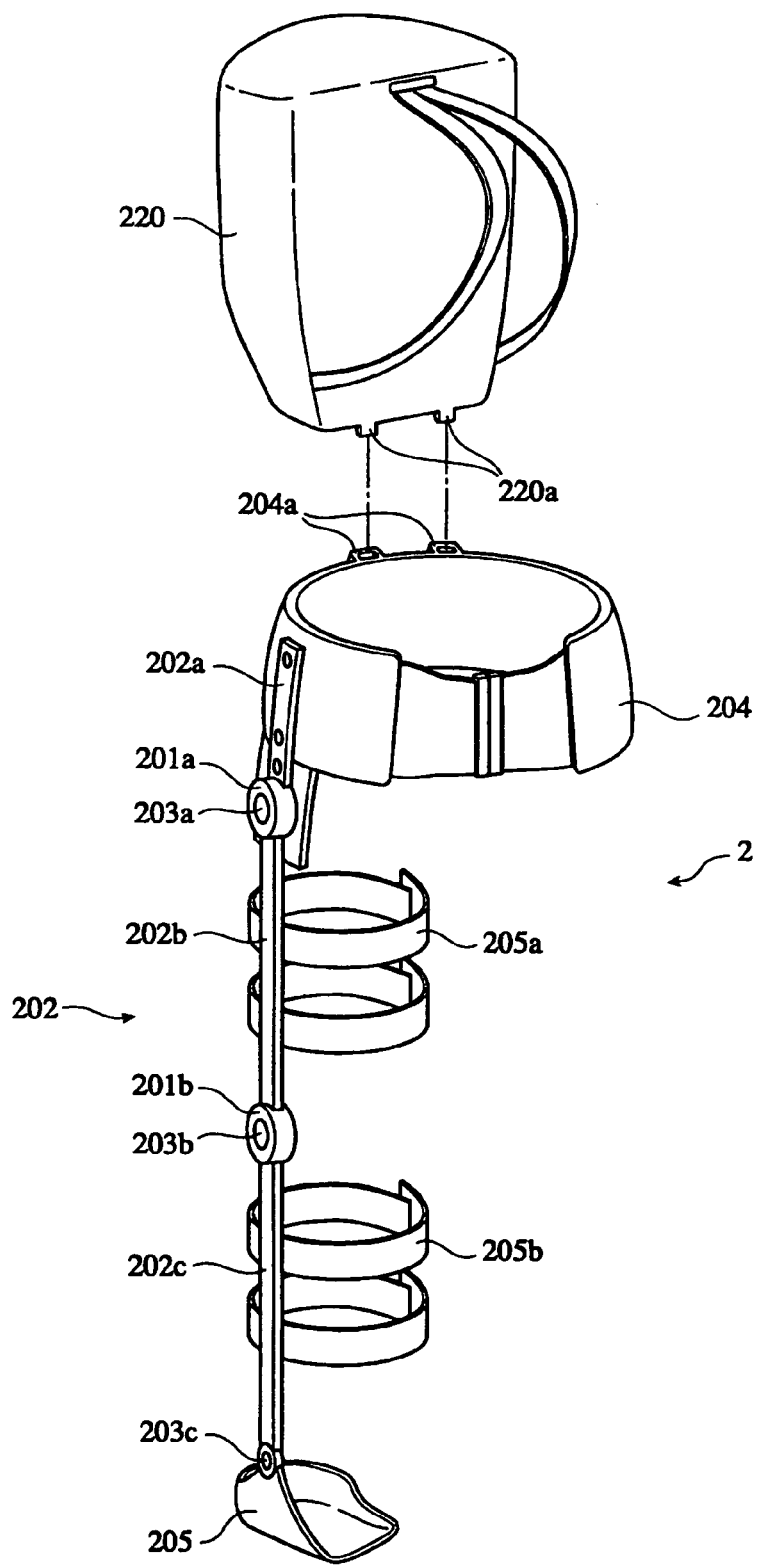
FIG. 2 is a perspective view showing the action-assist tool.

As shown in FIG. 2, the action-assist tool 2 comprises a waist joint 203*a* for coupling an upper arm 202*a* and a middle arm 202*b* rotatably, a knee joint 203*b* for coupling the middle arm 202*b* and a lower arm 202*c* rotatably, a heel joint 203*c* for coupling the lower arm 202*c* and a heel part 205 rotatably, an actuator 201*a* provided in the waist joint 203*a*, and an actuator 201*b* provided in the knee joint 203*b*. Fixtures 205*a* and 205*b*, such as a magic tape (registered trademark), which are fixed to the wearer's thigh and calf, are attached to the middle arm 202*b* and the lower arm 202*c*. Each of the actuators 201*a* and 201*b* includes a motor and a reduction gear.

The upper arm 202*a* is fixed to the waist part 204 which is wound around and fixed to the wearer's body. Projection parts 204*a* which are open to the top and the bottom are formed in the upper peripheral edge on the back side of the waist part 204, and bottom projections 220*a* of a bag 220 which accommodates the control device 20 and the power supply 21 are engaged with the openings of the projection parts 204*a*. Thus, the load of the bag 220 can be received by the waist part 204.

The heel part 205 is provided in an integral formation which fully covers the wearer's heel. A side wall of the heel part 205 is extended to be higher than the other side wall of the heel part 205, and the heel joint 203*c* is attached to the top end of the higher side wall. For this reason, all the loads of the action-assist tool 2 and the bag 220 are supported by the heel part 205, and are not applied to the wearer 1.

(2) Control System

Figure 3:
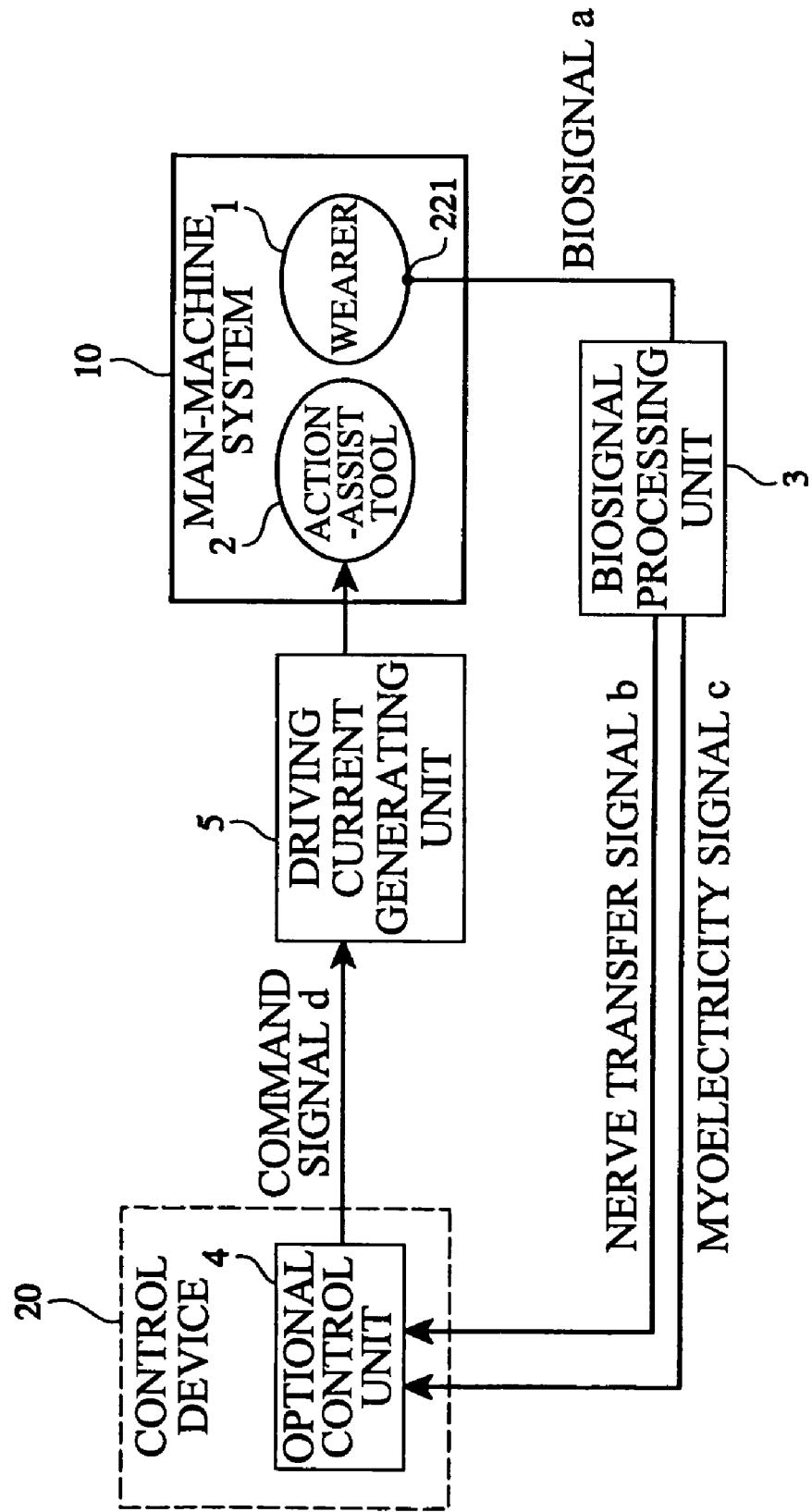
FIG. 3 is a block diagram showing the wearable action-assist device in the first embodiment.

FIG. 3 shows the control system of the wearable action-assist device of the first embodiment.

The wearer 1 and the action-assist tool 2 constitute a man-machine system 10. A control device 20 has an optional control unit 4. The biosignal sensor 221 which detects the wearer's biosignal a is connected to the input terminal of the optional control unit 4, and the driving current generating unit 5 is connected to the output terminal of the optional control unit 4. The driving current generating unit 5 is connected to the actuators 201*a* and 201*b* (which are collectively called the actuator 201) of the action-assist tool 2.

(a) Sensors

The wearable action-assist device of the first embodiment includes as the indispensable element the biosignal sensor 221 which detects the biosignal a from the wearer 1 in a state where the wearable action-assist device is worn by the wearer 1. The biosignal sensor 221 is usually attached to the wearer's skin. Alternatively, it may be embedded inside of the body.

In addition, as shown in FIG. 1, it is preferred that the wearable action-assist device of the first embodiment includes the barycenter sensor 222. Usually, a plurality of barycenter sensors 222 are attached to the sole of the wearer. It is possible to predict the direction of a motion of the human body by detecting which of the plurality of barycenter sensors 222 the relatively maximum weight is applied to.

Moreover, in order to raise the control accuracy, the wearable action-assist device of the first embodiment may be provided with the following: (1) the sensor for acquiring a signal which indicates the state of motion of the wearer 1, (for example, a force sensor, a torque sensor, a current sensor, an angle sensor, an angular velocity sensor, an acceleration sensor, a floor-reaction-force sensor, etc.); (2) the sensor for acquiring information on the external environment (for example, existence of an obstacle), (for example, a CCD, a laser sensor, an infrared sensor, an ultrasonic sensor, etc.); (3) the sensor for acquiring a biosignal other than the nerve transfer signal b and the myoelectricity signal c, (for example, a body temperature sensor, a pulse sensor, a brain-waves sensor, a cardiac potential sensor, a perspiration sensor, etc.). Since these sensors are publicly known, a description thereof will be omitted.

(b) The Biosignal Processing Unit

The biosignal a detected by the biosignal sensor 221 includes the nerve transfer signal b and the myoelectricity signal c. The nerve transfer signal b can also be called as an intention transfer signal. The nerve transfer signal b is provided such that (i) it precedes the head of the myoelectricity signal c (see FIG. 4), or (ii) it is superimposed with the head of the myoelectricity signal c (see FIG. 5).

Since the frequency of the nerve transfer signal b is generally higher than the frequency of the myoelectricity signal c, they can be separated from each other by using different band pass filters. The nerve transfer signal b can be acquired by using a band pass filter 32 of high bandwidth (for example, in a range from 33 Hz to several kilohertz) after the biosignal a is amplified by the amplifier 31. The myoelectricity signal c can be acquired by using a band pass filter 33 of middle bandwidth (for example, in a range from 33 Hz to 500 Hz) after the biosignal a is amplified by the amplifier 31.

Figure 4:
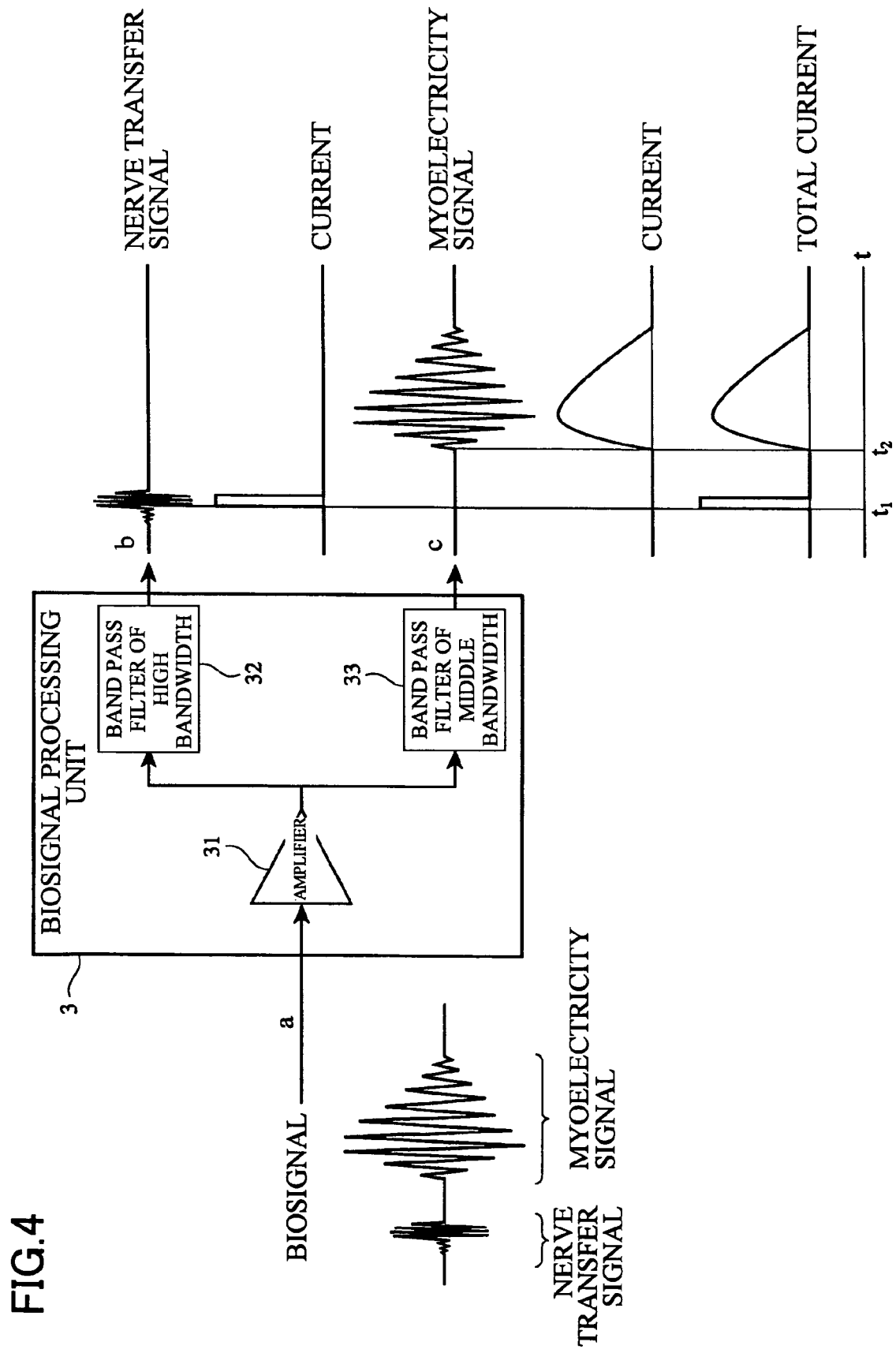
FIG. 4 is a diagram showing the composition of a biosignal processing unit and an example of processing of the biosignal (the nerve transfer signal and the myoelectricity signal are separated).
Figure 5:
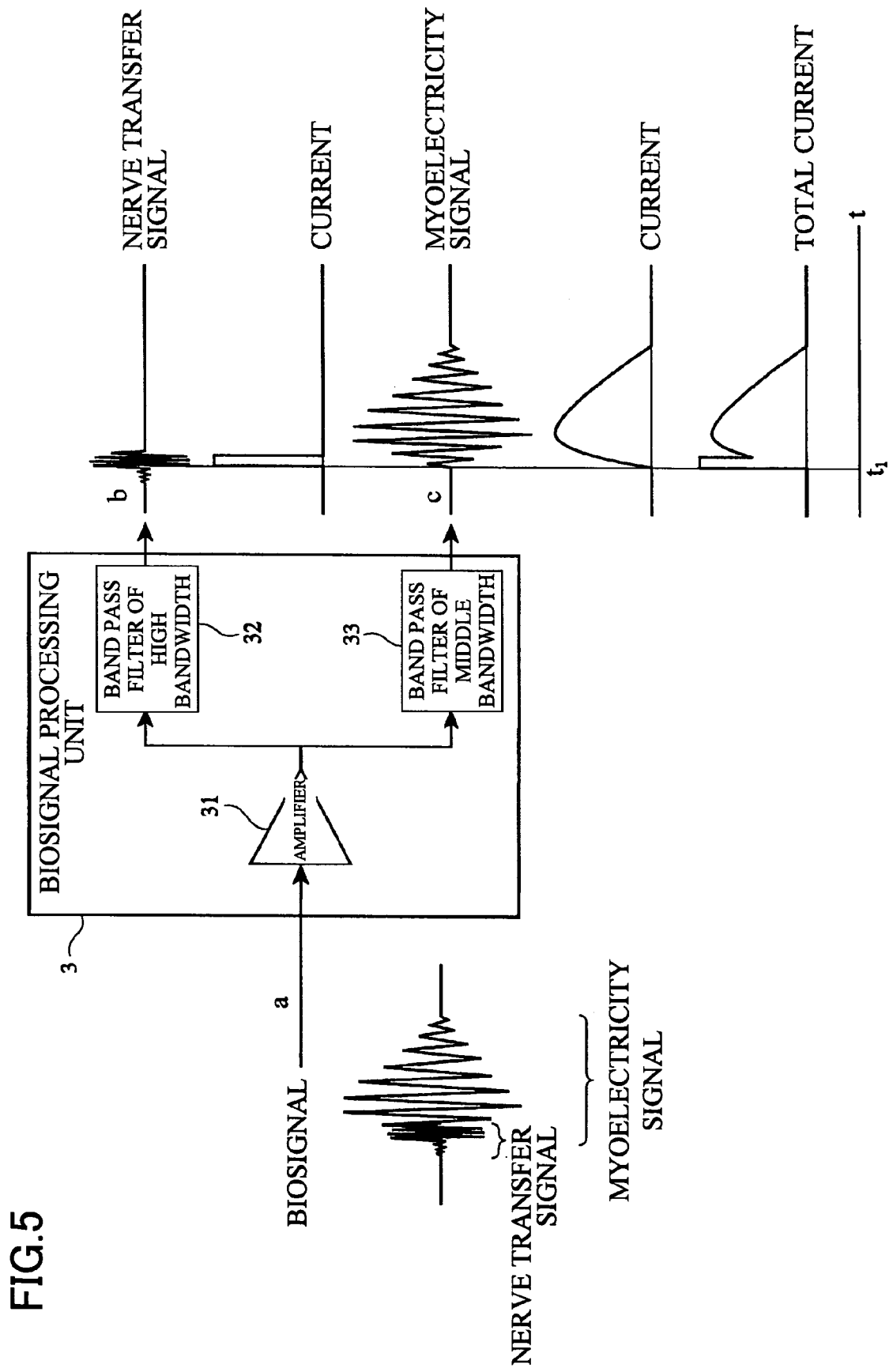
FIG. 5 is a diagram showing the composition of a biosignal processing unit and an example of processing of the biosignal (the nerve transfer signal and the myoelectricity signal are superimposed).

In FIG. 4 and FIG. 5, the filters are connected in parallel. The present invention is not limited to this embodiment. Alternatively, the filters may be connected in series. Moreover, the nerve transfer signal b may be superimposed not only with the head of the myoelectricity signal c but also with the subsequent part of the myoelectricity signal c. In such a case, what is necessary is just to use only the head part of the nerve transfer signal b for generation of a pulse current which will be mentioned later.

Smoothing processing is carried out to the nerve transfer signal b and the myoelectricity signal c. Each current shown in FIG. 4 and FIG. 5 is generated by the driving current generating unit 5 by inputting a command signal d, acquired by performing the smoothing of the signals from the biosignal processing unit 3, to the driving current generating unit 5.

As shown in FIG. 4, since the nerve transfer signal b has a narrow width and the nerve transfer signal b after the smoothing becomes a pulse-like shape, the current generated by the driving current generating unit 5 based on this nerve transfer signal b also becomes a pulse-like shape. The current (pulse current) acquired based on the nerve transfer signal b may be configured in the shape of a square wave.

On the other hand, as shown in FIG. 5, since the myoelectricity signal c has a wide width and the myoelectricity signal c after the smoothing becomes a crest-like shape which potential is substantially proportional to the myoelectricity, the current generated by the driving current generating unit 5 based on this myoelectricity signal c also becomes a crest-like shape.

When a total current of the pulse current generated based on the nerve transfer signal b and the current generated proportionally based on the myoelectricity signal c is supplied to the actuator 201, the actuator 201 generates a torque with the magnitude proportional to this total current. Since the total current is set up in each case of FIG. 4 and FIG. 5 so that it rises with a sufficiently large current, the actuator 201 is driven in accordance with the wearer's intention without delay, and the wearer 1 can perform operation according to his intention without giving the sense of incongruity to the wearer. Although the pulse current is shown in FIG. 4 and FIG. 5 as being so large, this is to emphasize the role of the pulse current. The illustration does not show the actual relation between the pulse current and the driving current acquired from the myoelectricity signal c. The magnitude of each current can be suitably set up by the feeling of the wearer 1 at the time of action.

(c) Optional Control Unit

The optional control unit 4 has a function which generates a command signal d for causing the actuator 201 to generate the power according to the wearer's intention, by using the nerve transfer signal b and the myoelectricity signal c. Proportional control is applicable to the optional control unit 4 as the control method being used. In accordance with the proportional control, the command signal value and the driving current value have a proportional relation, and the driving current value and the generating torque value of the actuator 201 have a proportional relation in accordance with the characteristics of the actuator 201. Therefore, a power assist rate is controllable to be a desired value by generating a predetermined command signal d using the optional control unit 4.

Alternatively, a combination of proportional control, derivative control, and/or integral control may be applied to the optional control unit 4 as the control method being used.

A power assist rate is a distribution ratio of the power generated by the wearer 1 and the power generated by the action-assist tool 2, and it is adjusted by manual operation or automatic operation. This power assist rate may have a negative value or a positive value. In case of a power assist rate having a positive value, the force generated by the action-assist tool 2 is added to the wearer's generating force. In a case of a power assist rate having a negative value, the force generated by the action-assist tool 2 is reduced from the wearer's generating force (namely, the load is put on the wearer 1), and the wearer 1 must generate a force that is larger than the usually generating force.

(d) Driving Current Generating Unit

When a command signal d from the optional control unit 4 is inputted, the driving current generating unit 5 generates, based on this command signal d, a current according to the nerve transfer signal b and a driving current according to the myoelectricity signal c, respectively, and supplies them to the actuator 201 to drive the actuator 201.

(B) Controlling Method and Controlling Program

Figure 6:
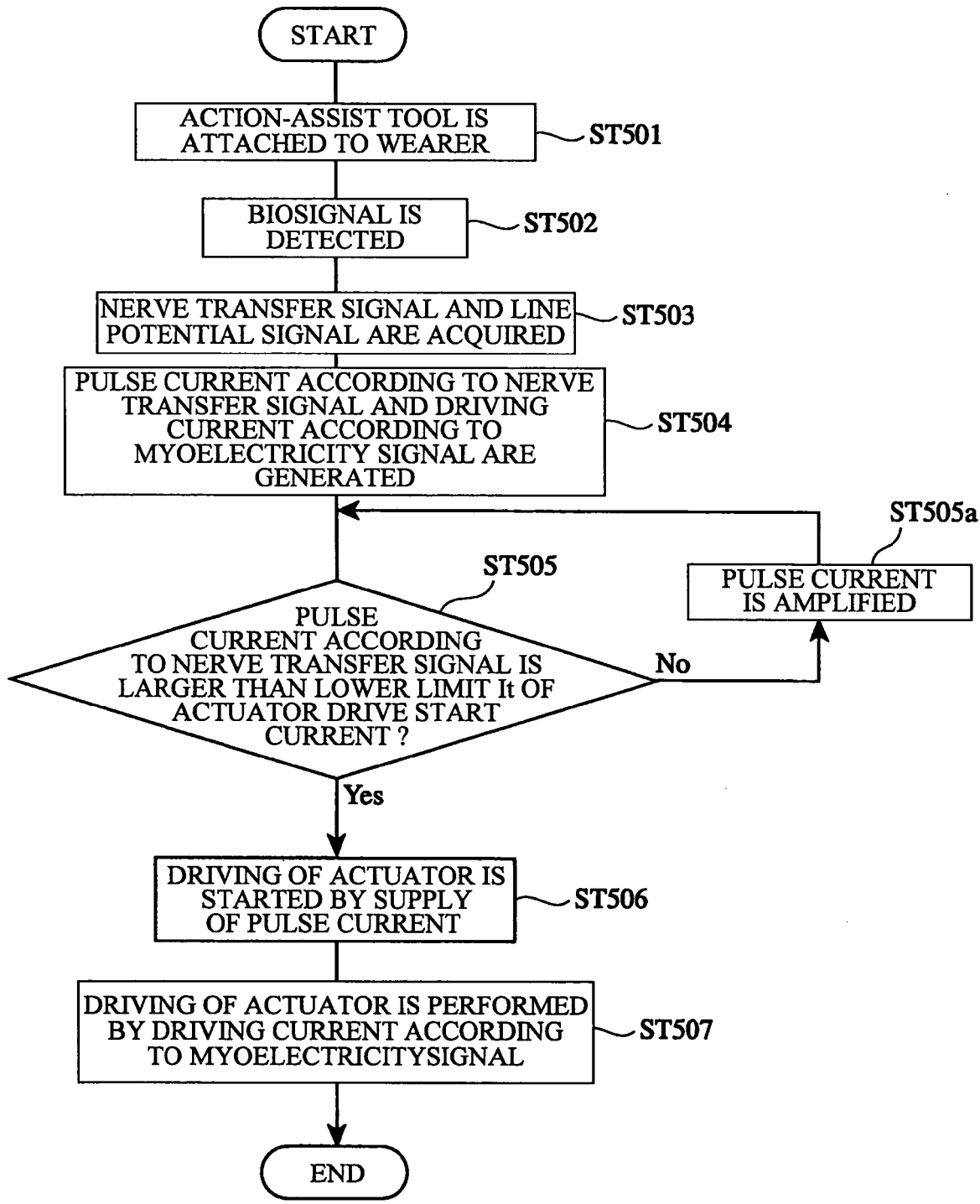
FIG. 6 is a flowchart for explaining the controlling method in a first embodiment of the invention.

FIG. 6 is a flowchart for explaining the controlling method of the first embodiment.

In a preferred example of the controlling method of the first embodiment shown in FIG. 6, the action-assist tool 2 having the actuator 201 which gives power to the wearer 1 is attached to the wearer 1 (ST501), and the wearer's biosignal a is detected (ST502).

As shown in FIG. 4 and FIG. 5, the nerve transfer signal b and the myoelectricity signal c are acquired from the biosignal a by using the biosignal processing unit 3 (ST503).

The optional command signal d1 for causing the actuator 201 to generate the power according to the wearer's intention is generated by using the acquired nerve transfer signal b and myoelectricity signal c (ST504). This optional command signal d1 is composed of a command signal d which generates the pulse current according to the nerve transfer signal b, and a command signal d which generates the driving current proportional to the myoelectricity signal c. By inputting each command signal d to the driving current generating unit 5, the current being supplied to the actuator 201 is generated by the driving current generating unit 5. Other signals (for example, signals acquired from the sensors other than the biosignal sensor 221 included in the first embodiment) may also be used instead for generation of the optional command signal d1. Also in the subsequent embodiments, unless otherwise specified, the other signals which are the same as mentioned above may be used instead.

The current that can drive the actuator 201 has a lower limit (threshold). When the pulse current according to the nerve transfer signal b (when the pulse current and the driving current are not superimposed), or the total current of the pulse current and the driving current (when the pulse current and the driving current are superimposed) is less than the lower limit, the pulse current is not useful for a quick drive start of the actuator 201, and the driving of the actuator 201 is not started until the driving current reaches the lower limit. Then, a considerable delay arises between the time of the wearer's cerebrum emission of the signal (the nerve transfer signal b) and the time of start of the action-assist device action. This will cause the sense of incongruity to be given to the wearer 1. In order to avoid the problem, it is desirable to start the driving of the actuator 201 immediately after the pulse current is generated according to the nerve transfer signal b.

Figure 7A:
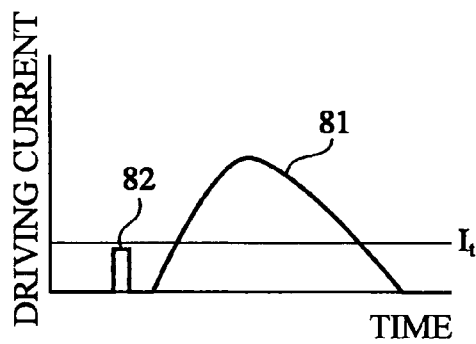
FIG. 7A and FIG. 7B are diagrams showing examples of the driving current acquired from the biosignal in which the nerve transfer signal and the myoelectricity signal are separated.
Figure 7B:
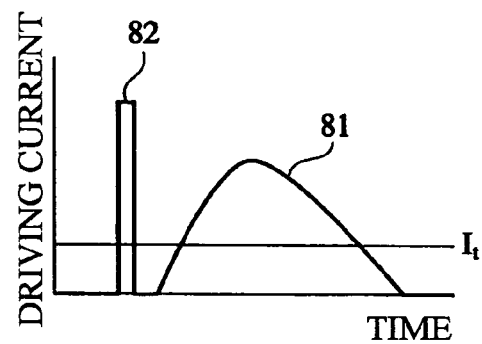

FIG. 7A and FIG. 7B show examples of the driving current acquired from the biosignal in which the nerve transfer signal and the myoelectricity signal are separated. In the driving current of FIG. 7A, the pulse current and the driving current are not superimposed and the pulse current is less than the lower-limit drive start current It. In the driving current of FIG. 7B, the pulse current in the state of FIG. 7A is amplified so that it may be larger than the lower-limit drive start current It.

Figure 8A:
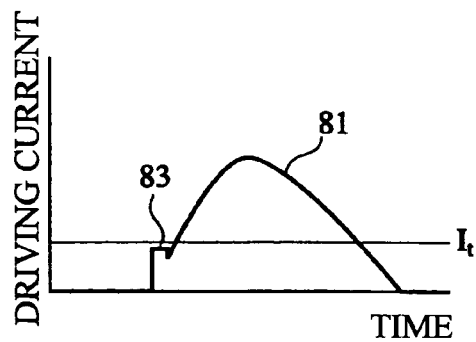
FIG. 8A and FIG. 8B are diagrams showing examples of the driving current acquired from the biosignal in which the nerve transfer signal and the myoelectricity signal are superimposed.
Figure 8B:
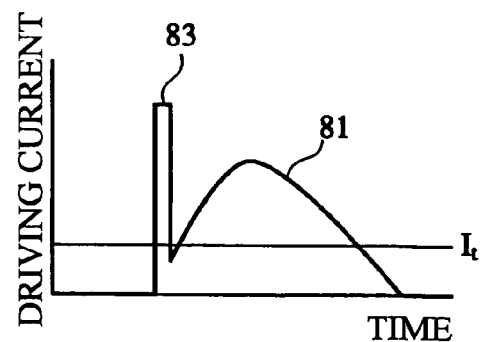

FIG. 8A and FIG. 8B show examples of the driving current acquired from the biosignal in which the nerve transfer signal and the myoelectricity signal are superimposed. In the driving current of FIG. 8A, the pulse current and the driving current are superimposed and the total current (equivalent to the current at the rising edge) is less than the lower-limit drive start current It. In the driving current of FIG. 8B, the total current in the state of FIG. 8A is amplified so that it may be larger than the lower-limit drive start current It.

Since the actuator 201 and each arm 202 and each joint 203 of the action-assist tool 2 have a moment of inertia, in order to perform assistance in accordance with the wearer's intention without delay, it is preferred to cause the actuator 201 to generate a torque with a quick rising edge. In order to realize this, in this embodiment, either when the pulse current 82 and the driving current 81 are not superimposed as shown in FIG. 7A, or when the pulse current 83 and the driving current 81 are superimposed as shown in FIG. 8A, if the pulse current 82 (or pulse current 83+driving current 81) is less than the lower-limit drive start current It of the actuator 201 (No in ST505), the pulse current 82 or 83 is amplified so that the amplified pulse current 82 (or amplified pulse current 83+driving current 81) is larger than the lower-limit drive start current It (ST505a). See FIG. 7B and FIG. 8B. In addition, the width of the pulse current 82 or 83 is enlarged, if needed, so that the actuator 201 can be certainly put into operation. It is made longer than the duration corresponding to the nerve transfer signal b. Accordingly, as a result, the driving of the actuator 201 can be started certainly by the supply of the pulse current 82 or 83 according to nerve transfer signal b (ST506).

In this way, after the driving of the actuator 201 is started, the actuator 201 is made to generate a driving torque so that it may be proportional to the driving current 81 according to the myoelectricity signal c (ST507). The power assistance of the action can be carried out according to the wearer's intention.

A controlling program for causing a computer to execute the above-mentioned controlling method may be stored in a storage device of the control device 20 of the wearable action-assist device. The above-mentioned controlling method comprises the step which detects the biosignal a (ST502), the step which acquires the nerve transfer signal b and the myoelectricity signal c from the biosignal a (ST503), the step which generates the optional command signal d1 for causing the actuator 201 to generate the power according to the wearer's intention, by using the acquired nerve transfer signal b and myoelectricity signal c (ST504), the steps which generate, based on the generated optional command signal d1, the pulse current according to the nerve transfer signal b and the driving current according to the myoelectricity signal c, respectively, and supply the respective currents to the actuator 201 (ST506, ST507). The control device 20 is, for example, constituted by a personal computer which is composed of a CPU, a storage unit, such as a hard disk or RAM, and an I/O device.

Although the control device 20 can be accommodated in the bag 220, it may be arranged outside the wearable action-assist device, if needed, and reception and transmission of signals between the control device 20 and the wearable action-assist device may be carried out by radio.

FIG. 9 shows an example of the composition which estimates the phase of the task from the physical quantity related to the action of the wearer 1, and causes the actuator to generate a power which meets a power assist rate corresponding to the estimated phase when performing the optional control of the actuator 201 in the wearable action-assist device of the first embodiment.

In the wearable action-assist device of FIG. 9, the elements which are essentially the same as corresponding elements in the wearable action-assist device of FIG. 3 are designated by the same reference numerals, and a description thereof will be omitted.

Before explaining the details of the wearable action-assist device of FIG. 9, a description will be given of tasks and phases. Each action pattern of the wearer is classified into tasks. Phases are a series of minimum action units which constitute each task.

Figure 10:
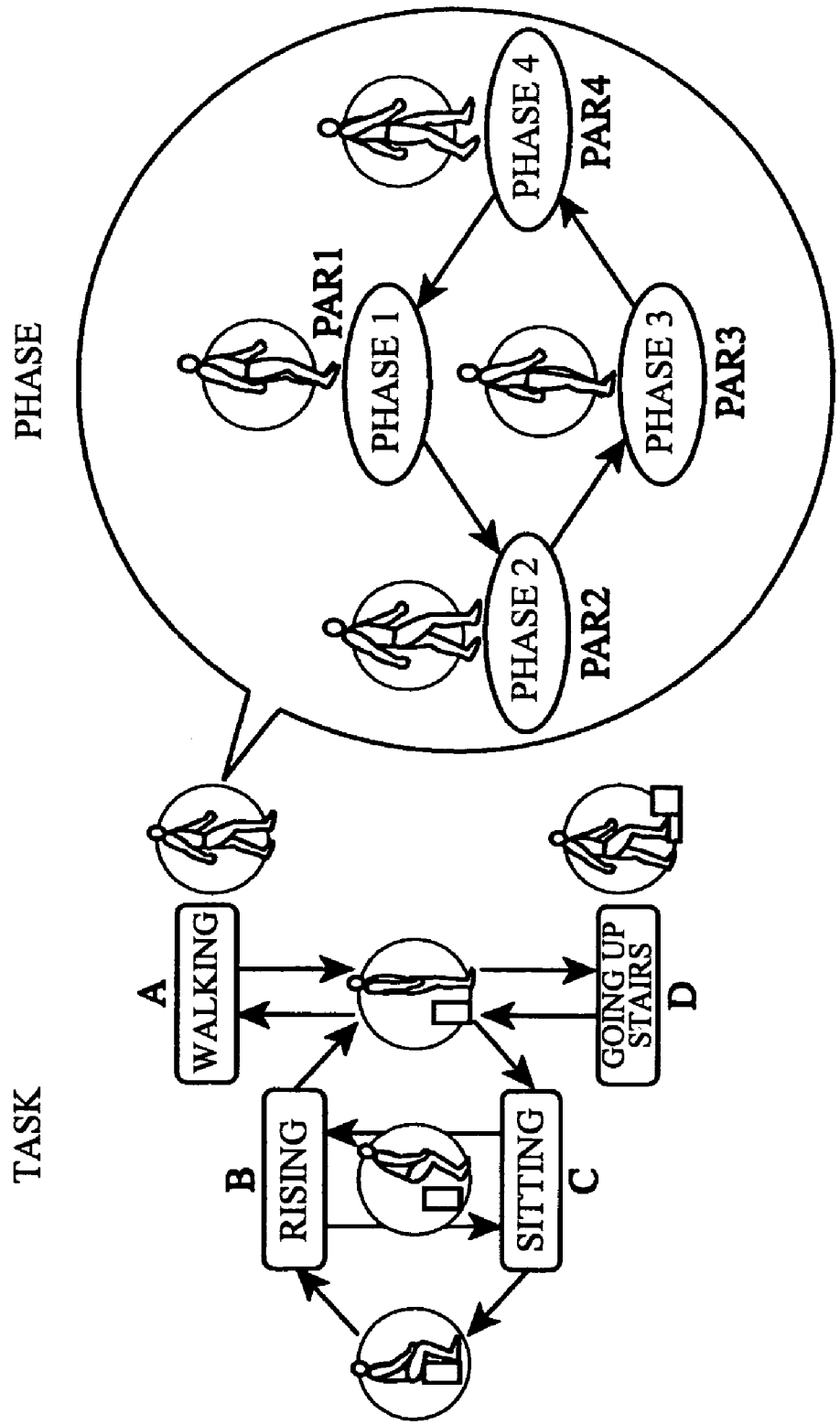
FIG. 10 is a diagram showing an example of tasks and phases.

FIG. 10 shows the human being's basic actions: walking (task A), rising (task B), sitting (task C), and going up or down stairs (task D). Naturally, the tasks are not necessarily limited to these tasks. Each task is composed of the phases. For example, the walking task A is composed of phase 1 in which the both legs align, phase 2 in which the right leg is forwarded, phase 3 in which the left leg is forwarded and the state where the both legs align is reached, and phase 4 in which the left leg is forwarded. Such a series of phases are called phase sequence. A suitable power for assisting the action of the wearer 1 differs depending on each of the series of phases. Therefore, the optimal assistance can be carried out for every phase by assigning different power assist rates PAR1, PAR2, PAR3 and PAR4 for the respective phases 1-4.

As a result of the analysis of actions of each person, it is turned out that the rotation angle and angular velocity of each joint, the walking speed and acceleration, the posture, and the movement of the center of gravity are determined for each phase. For example, a typical walking pattern of respective persons is determined, and when a person walks in that walking pattern, the most natural feeling arises. Therefore, what is necessary is to experientially determine each of rotation angles, angular velocities, etc. of each joint for all the phases of all the tasks, and store them in the database as standard parameters (reference rotation angle, reference angular velocity, etc.).

The wearable action-assist device of FIG. 9 comprises the man-machine system 10 which is composed of the wearer 1 and the action-assist tool 2, the biosignal processing unit 3 which acquires the nerve transfer signal b and the myoelectricity signal c from the wearer's biosignal a, and the database 6 in which the standard parameters of the respective phases and the power assist rates PAR assigned for the respective phases are stored. Moreover, the wearable action-assist device of FIG. 9 comprises: the optional control unit 14 which acquires the biosignal a (in which the nerve transfer signal b and the myoelectricity signal c are included) and the physical quantity (the rotation angle and angular velocity of each joint, the walking speed and acceleration, the posture, and the movement of the center of gravity etc. and, if needed, the signals from the other sensors) detected by the physical quantity sensor 13, and generates the optional command signal d (in which the power assist rate PAR etc. is included) which is acquired by comparing the acquired physical quantity with the standard parameter of the database 6; and the driving current generating unit 5 which generates the driving current, which is supplied to the actuator 201 of the action-assist tool 2, according to the command signal d of the optional control unit 14.

FIG. 11 is a diagram for explaining the process which estimates the phase of the task which the wearer 1 is trying to perform, by comparing a physical quantity with a standard parameter. FIG. 11 (a) shows a database of phases of each task for every action of the wearer. FIG. 11 (b) shows the changes of each of the knee rotation angle θ and its angular velocity θ', the waist rotation angle θ and its angular velocity θ', and the centroid position COG and its moving speed COG'. FIG. 11 (c) shows the state where all the phases (A1, A2, A3 . . . , B1, B2, B3 . . . , C1, C2, C3 . . . ) are taken out in a matrix formation.

The tasks and phases shown in FIG. 11 (a) are the same as those shown in FIG. 10. As illustrated, each of task A (walking), task B (rising), and task C (sitting) . . . is constituted by a series of phases (phase A1, phase A2, phase A3 . . . , phase B1, phase B-2, phase B3 . . . etc.), respectively.

When the wearer 1 starts action, the measured values of various kinds of physical quantities obtained by the physical quantity sensor 13 are compared with the standard parameters stored in database 6. The graphs of FIG. 11 (b) are used to show this comparison roughly. In the graphs, the knee rotation angle θ and its angular velocity θ', the waist rotation angle θ and its angular velocity θ', and the center of gravity COG and its moving speed COG', are shown respectively. Of course, the physical quantities for the comparison are not limited to these physical quantities.

At intervals of a short fixed period, the measured values of the physical quantities are compared with the standard parameters. This comparison is performed with respect to the series of phases in all the tasks (A, B, C . . . ). That is, as shown in FIG. 11 (c), all the phases (A1, A2, A3 . . . , B1, B2, B3 . . . , C1, C2, C3 . . . ) shown in FIG. 11 (a) are taken out in a matrix formation, and they are compares with the measured values of the physical quantities.

As shown in the graphs of FIG. 11 (b), if the comparison is performed for each of times t1, t2, t3 . . . , it is possible to identify the phase in which all the measured values of the physical quantities match with the standard parameters. What is necessary in order to eliminate the error of match is just to identify the phase after checking that the match takes place at a given number of times.

In the example of illustration, if the measured value matches with the standard parameter of phase A1 at a plurality of times, it is turned out that the current action is the action of phase A1. Of course, the phase having the standard parameter which matches with the measured value of the physical quantity is not necessarily the same as the initial phase (A1, B1, C1) of each task.

Figure 12:
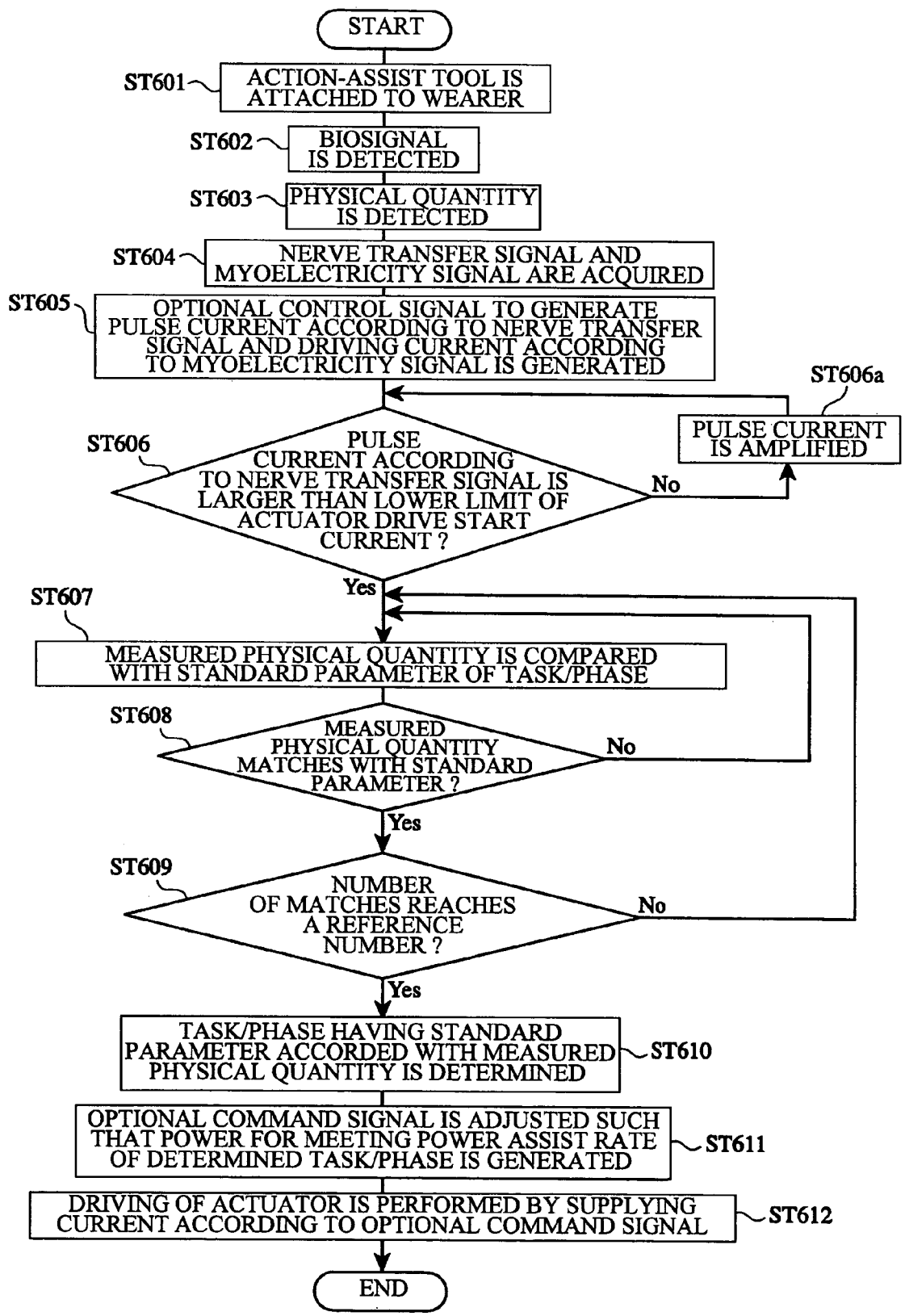
FIG. 12 is a flowchart for explaining the controlling method in which the power assist rate is controlled as a variation of the first embodiment.

FIG. 12 is a flowchart for explaining the controlling method in which the power assist rate PAR is controlled as a variation of the first embodiment. In FIG. 12, the steps ST601, ST602 and ST604-606 are substantially the same as the steps ST501-505a in FIG. 6, and a description thereof will be omitted. A description will be given of the process of the steps ST607-612.

The physical quantity sensor 13 detects the physical quantity of the man-machine system 10 (ST603). Although the physical quantity sensor 13 which detects the physical quantities, such as the rotation angle and angular velocity of each joint, the walking speed and acceleration, and the posture, is attached to the action-assist tool 2, it is preferred that the physical quantity sensor 13 which detects the physical quantity, such as the movement of the center of gravity, is attached directly to the wearer 1.

The physical quantities are sequentially compared with the respective standard parameters of the phases of the tasks stored in the database 6 one by one (ST607). As described above with reference to FIG. 11 (a) to (c), all the tasks and their phases are provided in a matrix formation. The comparison between the measured values of the physical quantities and the standard parameters of the respective phases is performed one by one in the sequence of A1, A2, and A3 . . . , B1, B2, and B3 . . . , C1, C2, and C3 . . . . Since the standard parameters are set up so as not to overlap between the phases of all the tasks (merely called "task/phase"), if the comparison is performed with the standard parameters of the phases of all the tasks, the phase of the task having the standard parameters which match with the measured values of the physical quantities can be determined (ST608).

Taking the error of each of the measured values of the physical quantities into consideration, a reference number of matches needed for the judgment is predetermined. When the number of matches reaches the reference number (ST609), the phase of the task corresponding to the measured values of the physical quantities is estimated (ST610). By referring to the database 6, the power assist rate PAR assigned to the phase corresponding to the action to be assisted is determined, and the above-mentioned optional command signal d is adjusted so that the actuator 201 may be driven to generate the power that meets the power assist rate PAR (ST611). The driving current generating unit 5 generates the current (the total current) according to the optional command signal d after the adjustment, and drives the actuator 201 by supplying the total current (ST612).

A controlling program for causing a computer to execute the above-mentioned controlling method may be stored in a storage device of the control device 20A of the wearable action-assist device. The above-mentioned controlling method comprises the step which detects the wearer's biosignal a (ST602), the step which detects the physical quantity of the man-machine system 10 (ST603), the step which estimates the phase which the wearer is trying to perform (ST610) by comparing the detected physical quantity with a standard parameter of each phase of each task (ST607-609), the step which generates the optional command signal d so that the actuator may be driven to generate the power which meets the power assist rate PAR according to the estimated phase (ST611), and the step which generates the current according to the optional command signal d to supply the current to the actuator (ST612).

As described in the foregoing, the optional command signal d is generated so that it may meet the power assist rate PAR optimized for every phase and the power application according to the optional command signal d is performed. Thus, it is possible to smooth assistance. And the driving of the actuator is started according to the pulse current according to the nerve transfer signal b. Thus, the driving of the actuator is started without delay and it is possible to perform assistance comfortably.

[2] Second Embodiment (A) Composition of Wearable Action-Assist Device

Figure 13:
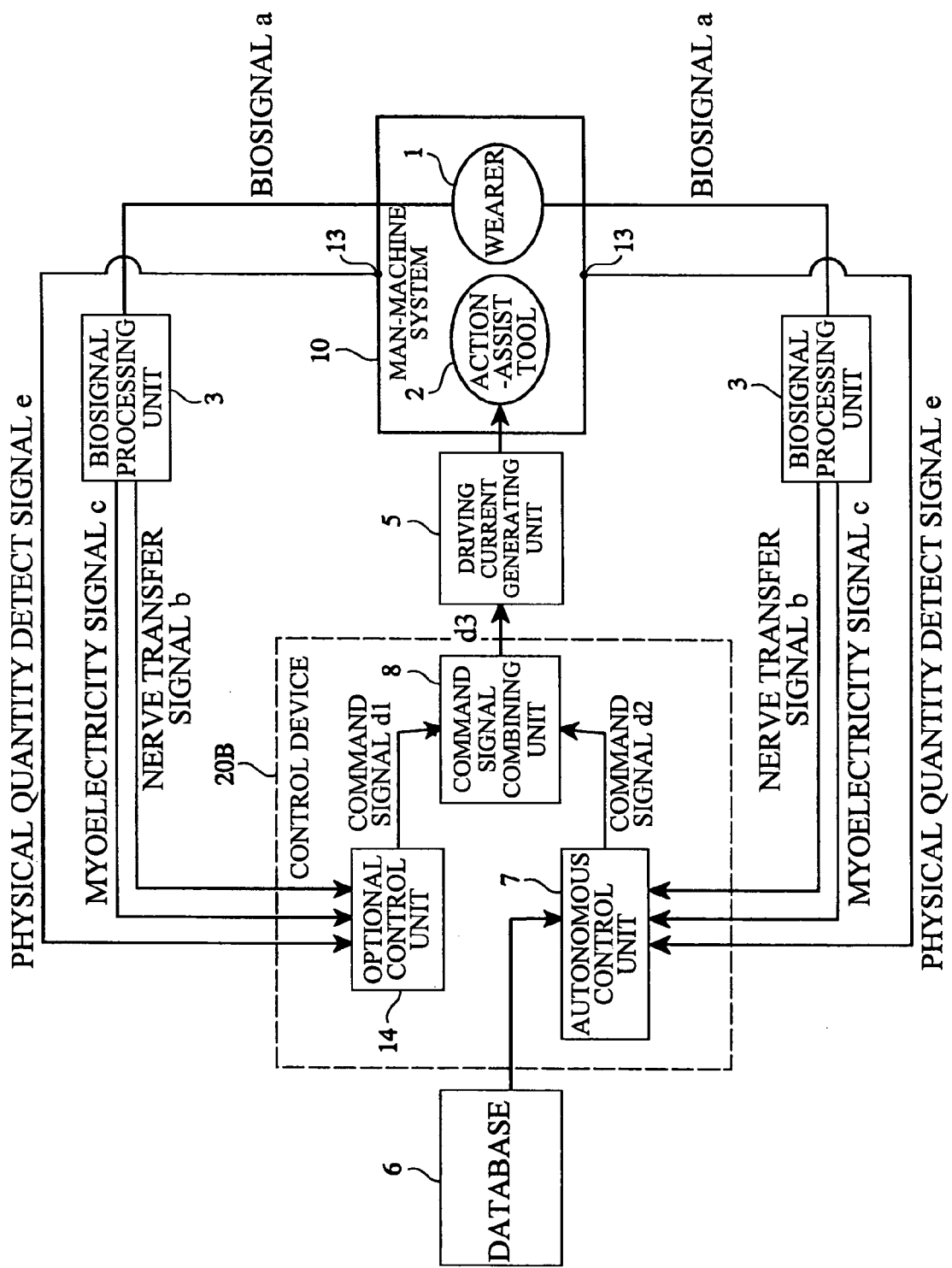
FIG. 13 is a block diagram showing the composition of a wearable action-assist device in the second embodiment of the invention.

As shown in FIG. 13, the wearable action-assist device of the second embodiment comprises the action-assist tool 2 having the actuator 201, the biosignal sensor 221 which detects the wearer's biosignal a, the physical quantity sensor 13 which detects the physical quantity of the man-machine system 10, and the optional control unit 14 which generates the command signal d (optional command signal d1) for causing the actuator 201 to generate the power according to the wearer's intention by using the biosignal a detected by the physical quantity sensor 13. Moreover, the wearable action-assist device of the second embodiment comprises the database 6 in which respective standard parameters of a series of minimum action units (phases) which constitute each action pattern of the wearer 1 classified as a task, the autonomous control unit 7 which estimates the phase of the wearer's task by comparing the physical quantity detected by the physical quantity sensor 13 with the standard parameter stored in the database 6, and generates the command signal d (autonomous command signal d2) for causing the actuator 201 to generate the power according to the estimated phase, the command signal combining unit 8 which combines the command signal d1 from the optional control unit 4 and the command signal d2 from the autonomous control unit 7, and the driving current generating unit 5 which generates the current according to the total command signal d3 combined by the command signal combining unit 8, to supply the current to the actuator 201.

The optional control unit 14 may be the same as the optional control unit 4 of the first embodiment shown in FIG. 3. Specifically, as shown in FIG. 4 and FIG. 5, it is preferred that the optional control unit 14 generates the optional command signal d1 according to the nerve transfer signal b and the myoelectricity signal c, and uses the pulse current according to the nerve transfer signal b as a trigger signal for starting the driving of the actuator 201.

As shown in FIG. 10 and FIG. 11 (a)-(c), the autonomous control unit 7 has a function which estimates the phase of the wearer's task by comparing the physical quantity detected by the physical quantity sensor 13 with the standard parameter of each phase of each task stored in the database 6, and generates the autonomous command signal d2 for causing the actuator 201 to generate the power according to the estimated phase. Therefore, the explanation of FIG. 10 and FIG. 11 (a)-(c) is applicable to the autonomous control unit 7 as it is.

The command signal combining unit 8 combines the optional command signal d1 from the optional control unit 14 and the autonomous command signal d2 from the autonomous control unit 7. For example, in autonomous control, a fixed power is given for every phase. Therefore, the combined command signal d3 has a waveform which causes the actuator 201 to generate the resulting power which is obtained by adding the power according to the optional control which changes from the beginning to the end, to the fixed power according to the autonomous control which is fixed for every phase. The effect of the combination of the command signals will be explained later.

(B) Controlling Method and Controlling Program

Figure 14:
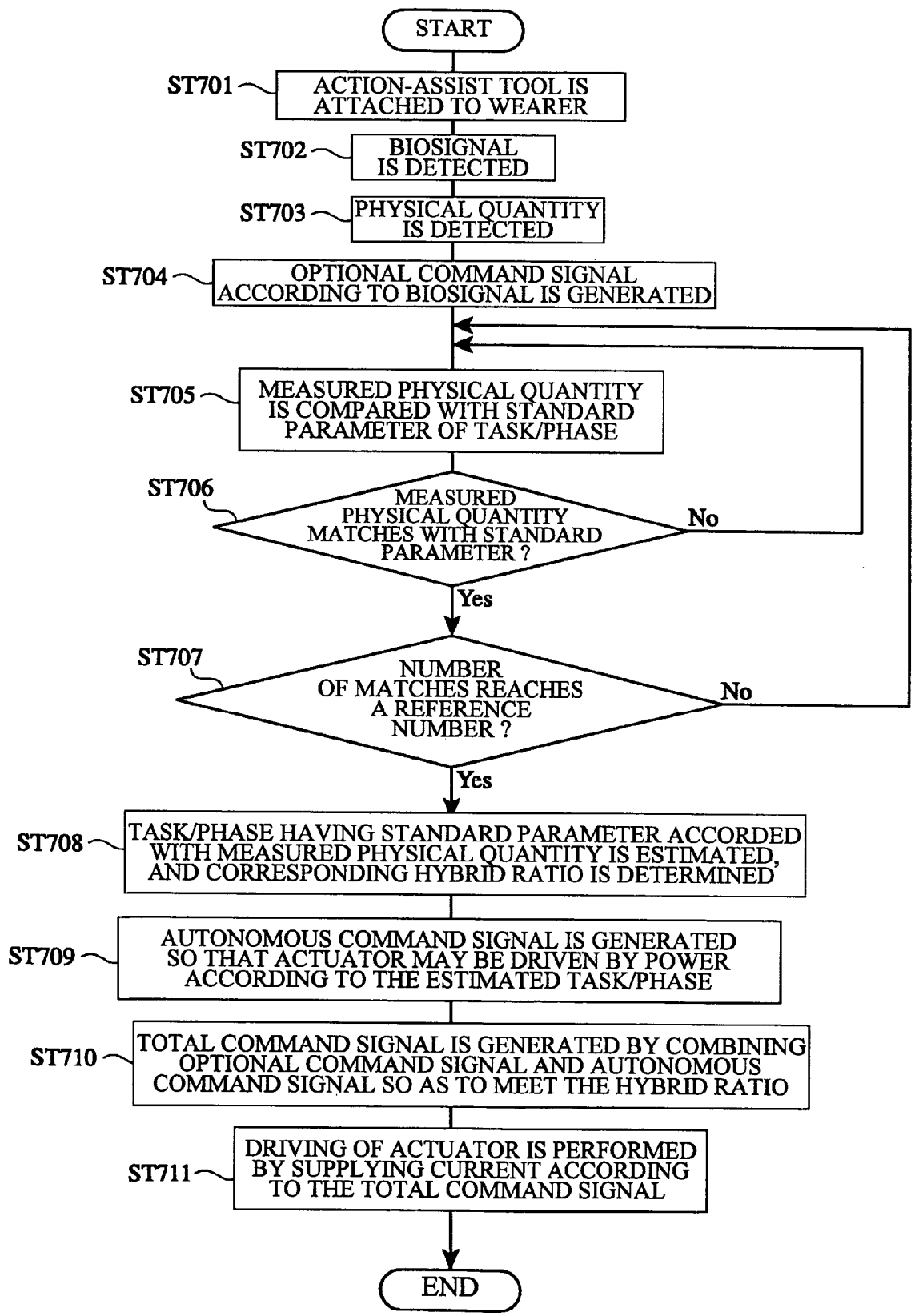
FIG. 14 is a flowchart for explaining the controlling method of the second embodiment.

FIG. 14 is a flowchart which shows the controlling method of the second embodiment.

As shown in FIG. 14, in the controlling method, the action-assist tool 2 having the actuator 201 which gives power to the wearer 1 is attached to the wearer 1 (ST701). The wearer's 1 biosignal a is detected (ST702), and the physical quantity of the man-machine system 10 which is composed of the wearer 1 and the action-assist tool 2 is detected (ST703).

The optional command signal d1 for causing the actuator 201 to generate the power according to the wearer's intention by using the detected biosignal a is generated (ST704). The detected physical quantity is compared with the standard parameter of each phase of each task stored in the database 6 (ST705-707). The phase of the task of the wearer 1 is estimated by the comparison result, and the hybrid ratio α corresponding to the estimated phase of the task (optional command signal d1/autonomous command signal d2) is determined (ST708).

And the autonomous command signal d2 for causing the actuator 201 to generate the power according to this phase is generated (ST709). The optional command signal d1 and the autonomous command signal d2 are combined to meet the hybrid ratio α, and the total command signal d3 is generated (ST710). The actuator 201 is driven by supplying to the actuator 201 the current which is generated according to this total command signal d3 (ST711).

In the flowchart of FIG. 14, the steps ST701-703 and ST705-708 are the same as the steps ST601-603 and ST607-610 in the flowchart of the first embodiment shown in FIG. 12, respectively. And it is preferred that the step (ST704) which generates the optional command signal d1 according to the biosignal a is composed of the steps ST604-606a shown in FIG. 12.

And it is preferred that the optional command signal d1 is for generating the pulse current according to the nerve transfer signal b and the driving current according to the myoelectricity signal c, similar to the first embodiment. The hybrid ratio α is predetermined for every phase of each task so that the action of the wearer 1 can be assisted comfortably, and they are stored in the database 6. When the estimation of a phase is performed by the comparison of the physical quantity and the standard parameter, the control device 20A automatically determines this hybrid ratio α as mentioned above. As a result, the total command signal d3 is generated so that it may meet the determined hybrid ratio α, and the application of power according to this total command signal d3 allows the wearable action-assist device to perform smoothly assistance according to each of various actions.

The step which detects the wearer's biosignal a in order to perform the above-mentioned control (ST702), the step which detects the physical quantity of man-machine system 10 which is composed of the wearer 1 and the action-assist tool 2 (ST703), the step which generates the optional command signal d1 for causing the actuator 201 to generate the power which followed the wearer's intention using detected biosignal a (ST704), while estimating the phase of the task of (ST 705-707) and the wearer 1 by comparing the physical quantity and the standard parameter of each phase of each task which were detected, the step which specifies hybrid ratio α corresponding to this phase (ST708), the step which generates the autonomous command signal d2 for causing the actuator 201 to generate the power according to this phase (ST709), the step which combines optional command signal d1 and the autonomous command signal d2, and generates the total command signal d3 so that it may become specified hybrid ratio α (ST710), the program for control to which the step (ST711) which drives actuator 201 by supply of the current generated according to the generated total command signal d3 is made to perform is stored in the storage apparatus of control device 20B of wearable action-assist device.

Figure 15:
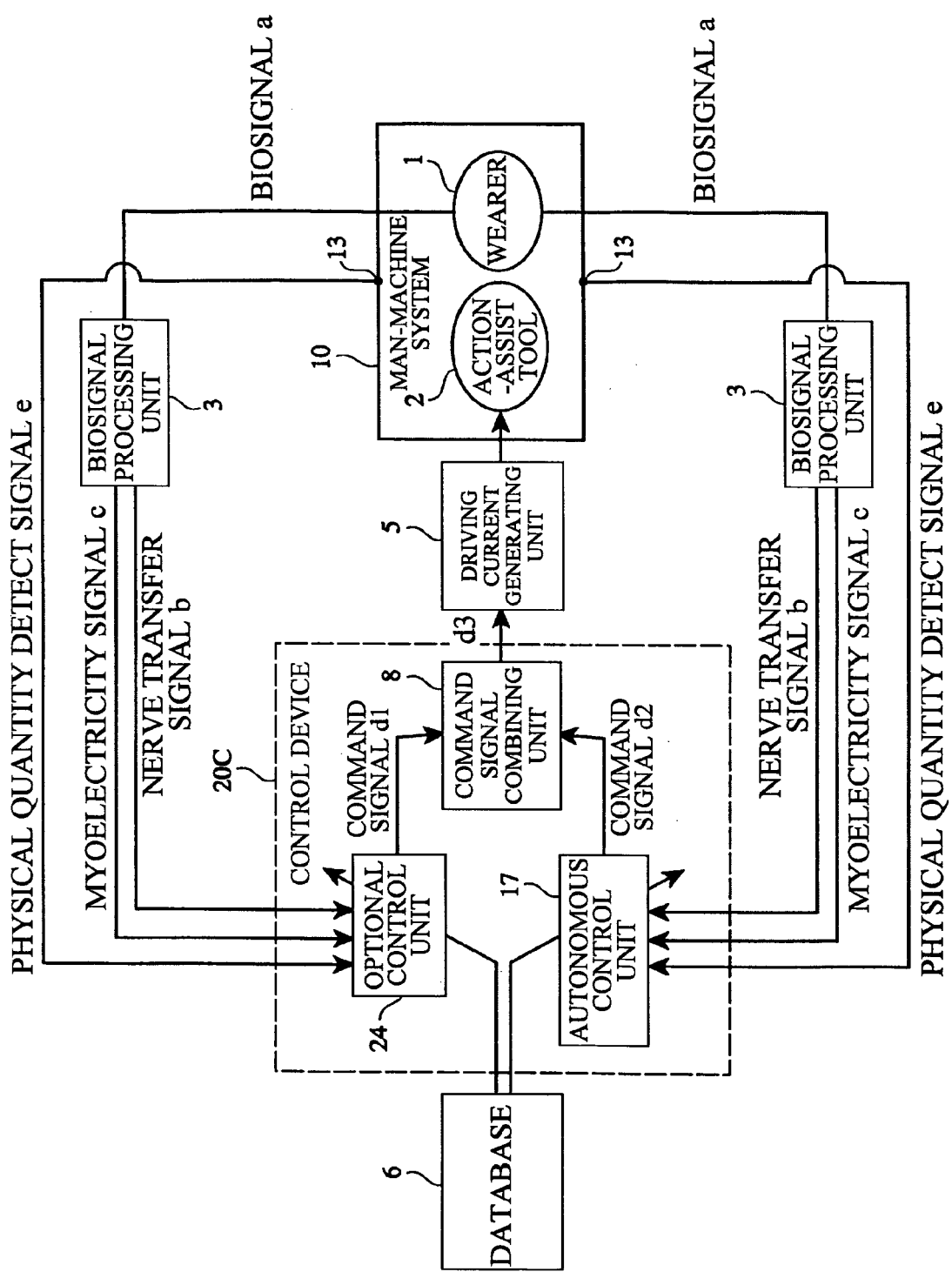
FIG. 15 is a block diagram showing an example of the composition which controls a power assist rate in the wearable action-assist device of the second embodiment.

FIG. 15 is a block diagram showing another example of the wearable action-assist device of the second embodiment.

As shown in FIG. 15, the wearable action-assist device of this embodiment comprises the action-assist tool 2 with actuator 201 which gives power to the wearer 1, the biosignal sensor 221 which detects the wearer's biosignal a, the physical quantity sensor 13 which detects the physical quantity related to the action of the wearer 1, the optional control unit 24 which generates the command signal d for causing the actuator 201 to generate the power according to the intention of wearing 1 using biosignal a detected by biosignal sensor 221 (optional command signal d1), the database 6 which stored each standard parameter of a series of minimum action units (phase) which constitute each pattern of the wearer 1 classified as a task, the wearer's 1 pattern is estimated by comparing the physical quantity and the standard parameter which were detected by physical quantity sensor 13, the autonomous control unit 17 which generates the command signal d for causing the actuator 201 to generate the power according to the autonomous command signal d2, the command signal combining unit 8 which combines optional command signal d1 and autonomous command signal d2, and the driving current generating unit 5 which generates the current according to the total command signal d combined by the command signal combining unit 8, to supply the current to the actuator 201.

It is preferred to acquire, from the biosignal a, the nerve transfer signal b for operating the wearer's muscular line skeletal system and the myoelectricity signal c accompanied with the wear's muscular line activity. For this purpose, the biosignal processing unit 3 similar to the first embodiment may be used, and a description thereof will be omitted. Although the two units are shown in FIG. 15, a single unit being shared to attain the purpose may be used instead. The database 6, the autonomous control unit 17, the command signal combining unit 8, and the driving current generating unit 5 are essentially the same as corresponding elements in FIG. 13. The optional control unit 24 and autonomous control unit 17 by comparing the physical quantity detected by physical quantity sensor 13 with the standard parameter stored in the database 6, the phase of the task which the wearer 1 is trying to perform is estimated, and it has a function which generates optional command signal d1 and autonomous command signal d2 so that it may be set to the hybrid ratio α according to this phase, and the power assist rate PAR.

Figure 16:
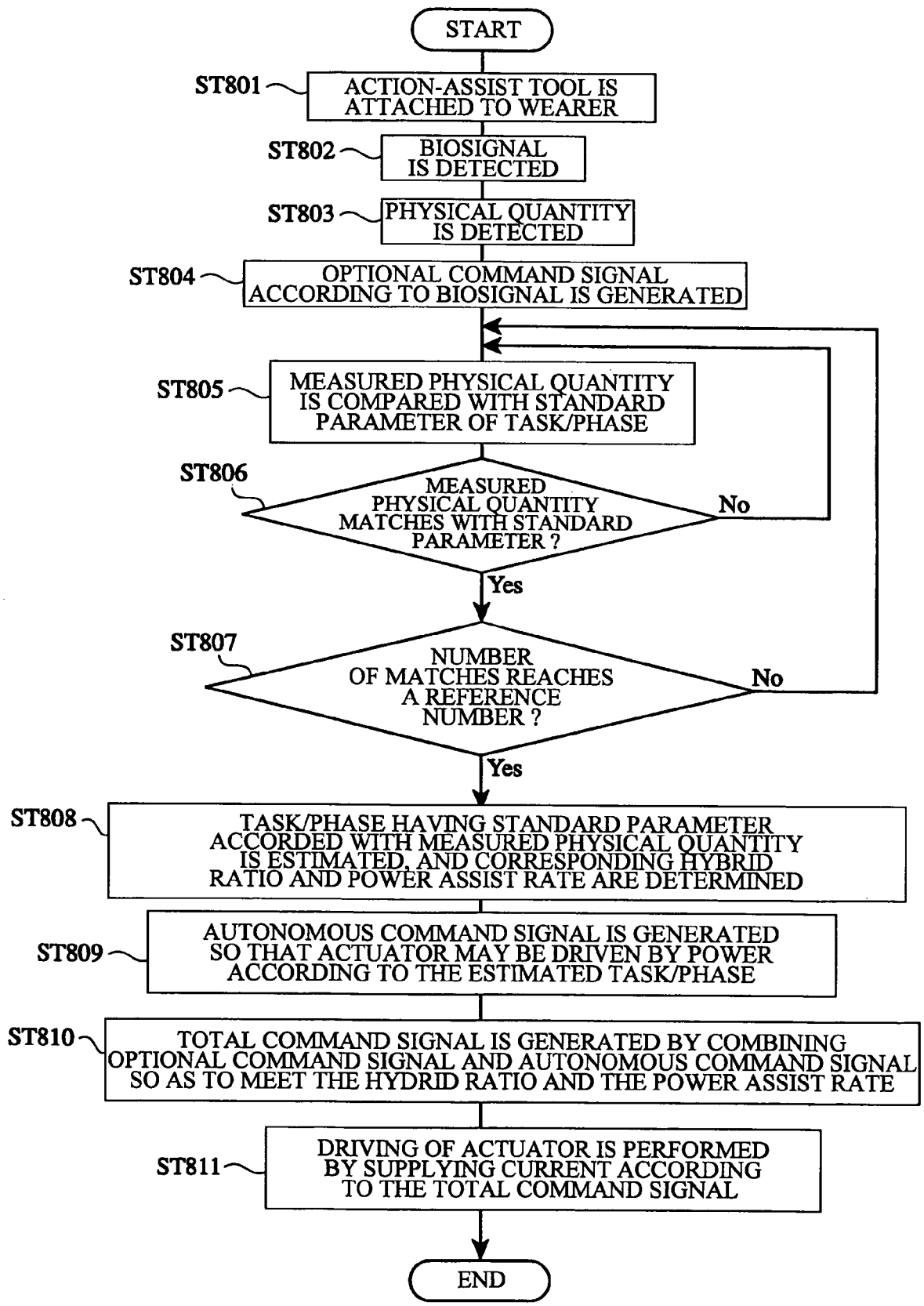
FIG. 16 is a flowchart for explaining control of a power assist rate in the controlling method of the second embodiment.
Figure 17:
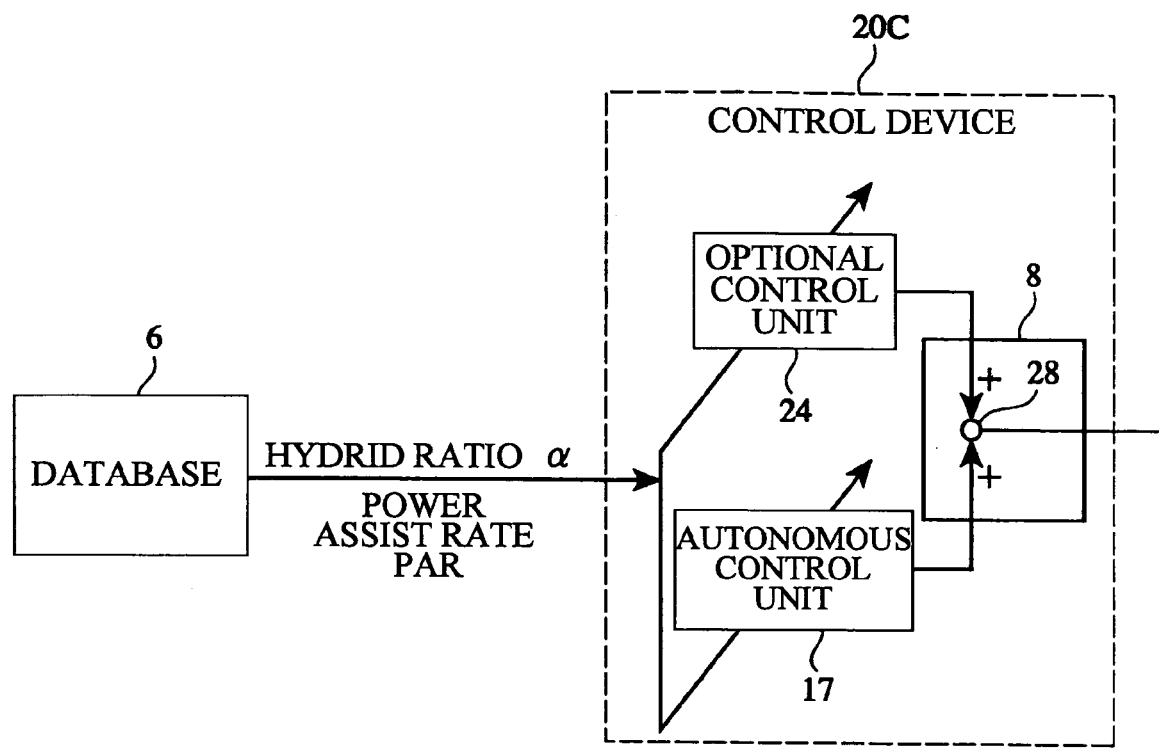
FIG. 17 is a block diagram showing the composition of the control unit of the second embodiment.

FIG. 16 is a flowchart for explaining the controlling method in which the power assist rate is controlled in the wearable action-assist device of this embodiment. FIG. 17 is a block diagram showing the composition of the control unit of the second embodiment.

As shown in FIG. 16 and FIG. 17, in this controlling method, the action-assist tool 2 having the actuator 201 which gives power to the wearer 1 is attached to the wearer 1 (ST801). The wearer's biosignal a is detected (ST802), the physical quantity of the man-machine system 10 which is composed of the wearer 1 and the action-assist tool 2 is detected (ST803), and the optional command signal d1 according to the detected physical quantity is generated (ST804).

While presuming the phase of the task which (ST 805-807) and the wearer 1 are trying to perform by comparing the detected physical quantity with the standard parameter of each phase stored in database 6, the hybrid ratio α corresponding to this phase and the power assist rate PAR are specified (ST808), and the autonomous command signal d2 for driving actuator 201 under the power according to this phase is generated (ST809).

And the optional command signal d1 and the autonomous command signal d2 are combined, and the total command signal d3 is generated so that it may meet the determined hybrid ratio α and power assist rate PAR (ST810). The actuator 201 is driven by supply of the current generated according to this total command signal d3 (ST811).

The step which detects the wearer's biosignal a in order to perform the above-mentioned control (ST802), the step which detects the physical quantity of man-machine system 10 which is composed of the wearer 1 and the action-assist tool 2 (ST803), the step which generates the optional command signal d1 for causing the actuator 201 to generate the power according to the wearer's intention using detected biosignal a (ST804), while presuming the phase which (ST 805-807) and the wearer 1 are trying to perform by comparing the physical quantity and the standard parameter of each phase which are detected, the step which specifies the hybrid ratio α corresponding to the phase of this task, and the power assist rate PAR (ST808), so that it may be set to the step (ST809) which generates the autonomous command signal d2 for causing the actuator 201 to generate the power according to the phase of this task, and the specified hybrid ratio α and power assist rate PAR, the step (ST810) which combines optional command signal d1 and the autonomous command signal d2 and generates the total command signal d3, and the step (ST811) which drives actuator 201 by supply of the current generated according to the generated total command signal d3 are made to perform, are included in the controlling program which is stored in the storage device of the control device 20C of the wearable action-assist device.

[3] Other Functions

Drive Control at the Time of Starting (1) In the Case of Reflective Action

Figure 18A:
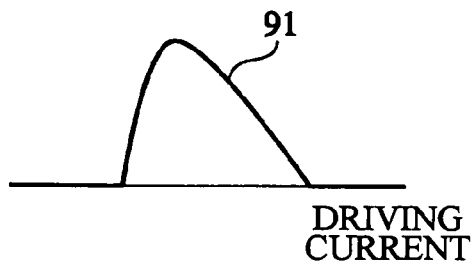
FIG. 18A and FIG. 18B are diagrams showing an example of the modification of driving current generation.
Figure 18B:
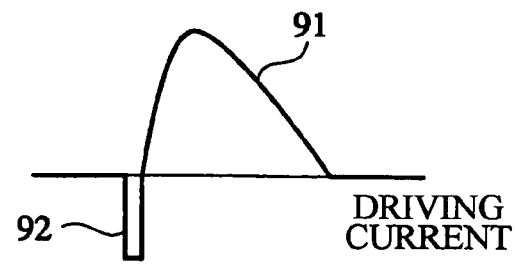

For example, when pushed suddenly from behind, it is necessary to forward one leg reflectively and to support the body, in order to avoid falling to the ground. If control of forwarding one leg is merely performed, it causes the leg to be pushed in front suddenly and the wearer stretches the leg instinctively. The wearer's operation of forwarding one leg will become awkward. In such a case, as shown in FIG. 18A, when supplying the current 91 which makes the actuator 201 drive in the direction, the current 92 of a short-time (ranging from 0.01 to 0.3 seconds) in the opposite direction is supplied just before supplying the current 91 as shown in FIG. 18B, so that the actuator 201 is driven in the opposite direction. The wearer 1 will try to forward one leg reflectively, so the operation will become rather smooth. The control using such reflexes cannot be adapted for the usual robot, and it demonstrates an effect for the first time in the case of the wearable action-assist device of this invention which is attached to the wearer 1

(2) In the Case of the Usual Action

When autonomous control which raises a leg is performed also in the case of usual operation like a walk, it may become the touch which had the leg pushed suddenly. If the current 91 which makes the actuator 201 drive in the direction is supplied after that which supplies current 92 of a counter direction too at the time of starting, and makes a counter direction drive actuator 201 in order to remove such sense of incongruity, a comfortable smooth motion can be carried out.

Some examples of the present invention will now be described. However, the present invention is not limited to these examples.

Example 1

Figure 19:
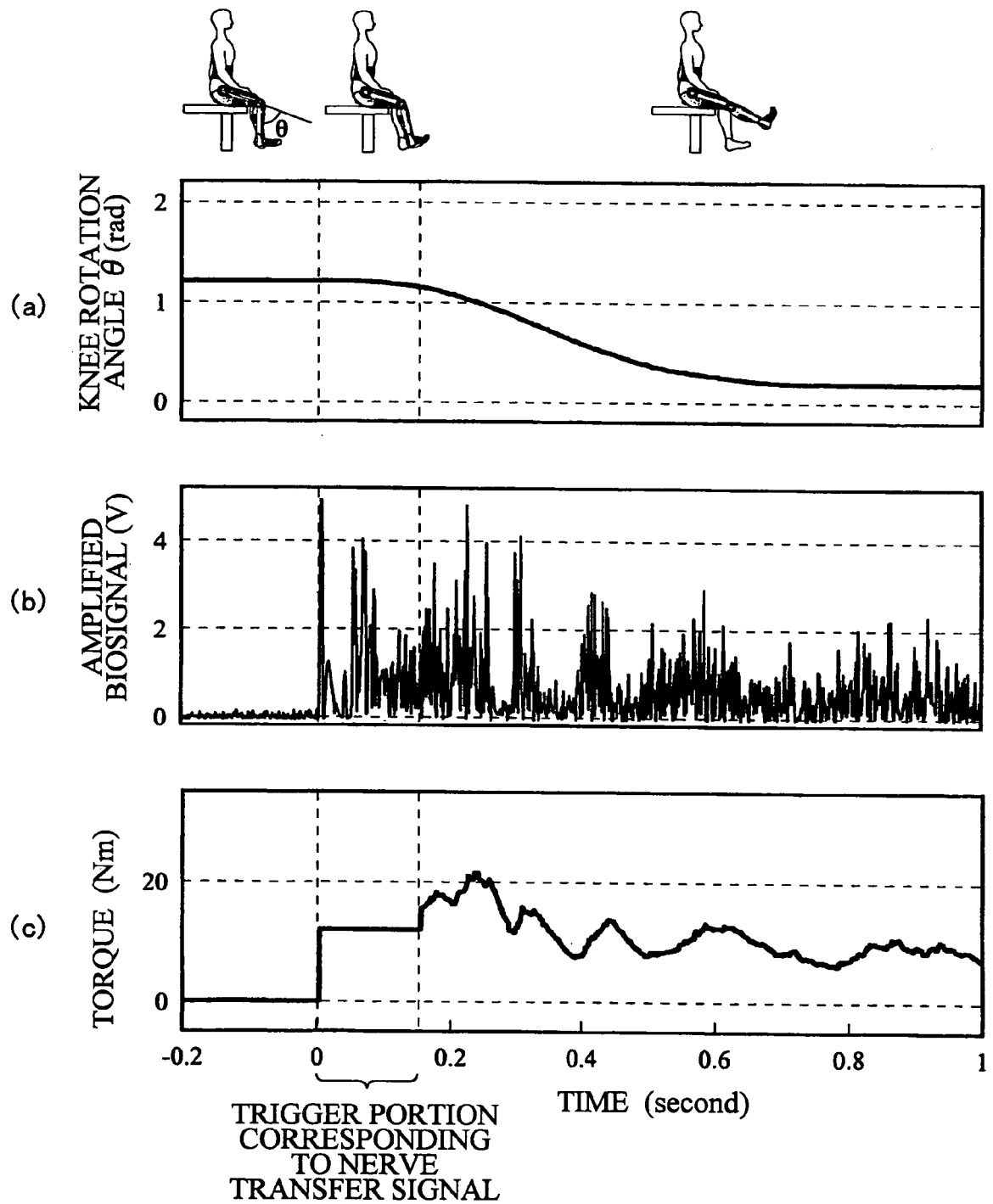
FIG. 19 is a diagram showing an experimental result when applying the pulse current according to the nerve transfer signal in the example 1.

FIG. 19 shows the experimental result when applying the pulse current according to the nerve transfer signal in the example 1. FIG. 19 (a) shows the change of the knee rotation angle θ, FIG. 19 (b) shows the change of the biosignal which is amplified, and FIG. 19 (c) shows the change of the torque of the knee actuator.

Figure 20:
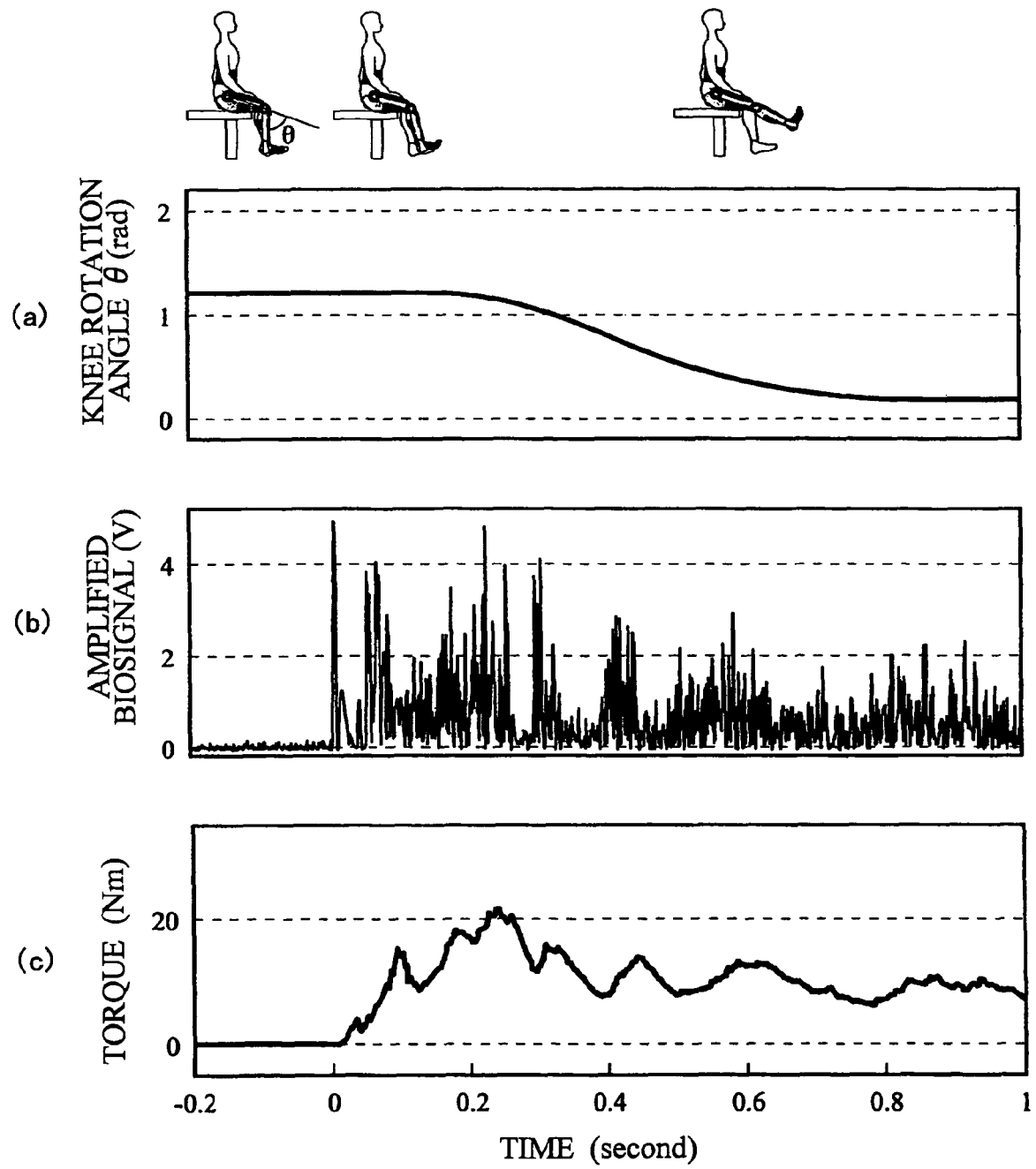
FIG. 20 is a diagram showing an experimental result when not applying the pulse current according to the nerve transfer signal in the example 1.

FIG. 20 shows the experimental result when not applying the pulse current according to the nerve transfer signal in the example 1. FIG. 20 (a) shows the change of the knee rotation angle θ, FIG. 20 (b) shows the change of the biosignal which is amplified, and FIG. 20 (c) shows the change of the torque of the knee actuator.

This example is for explaining the effect of the first embodiment. When the wearer performs expansion action of the knee joint from the state in which the wearer relaxes and sits on the chair, the torque of the knee actuator 201b is measured respectively under the conditions for using the nerve transfer signal b as a trigger signal (refer to FIG. 19 (a)-(c)), and under the conditions for not using the nerve transfer signal b as a trigger signal (refer to FIG. 20 (a)-(c)) (i.e., the conditions in which only the driving current according to the myoelectricity signal c is supplied to the actuator 201b).

In the case of the former conditions (refer to FIG. 19 (c)), the torque was obtained in which the pulse current of the predetermined magnification corresponding to the nerve transfer signal b is superimposed at the front edge of the torque obtained from the detected biosignal a. The change of the knee rotation angle θ was started 0.2 seconds after the detection of the biosignal a.

On the other hand, in the case of the latter conditions (refer to FIG. 20 (c)), the torque in the state that is the same as the waveform of the biosignal a was obtained. Since the rise of this torque was loose, it took 0.3 second from the detection of the biosignal a to start the change of the knee rotation angle θ.

From these results, it is found out that the driving of the actuator 201b can be started quickly by using the nerve transfer signal b as a trigger signal and supplying the pulse current (square wave) having a predetermined width corresponding to the front edge of the biosignal a.

Example 2

Figure 21:
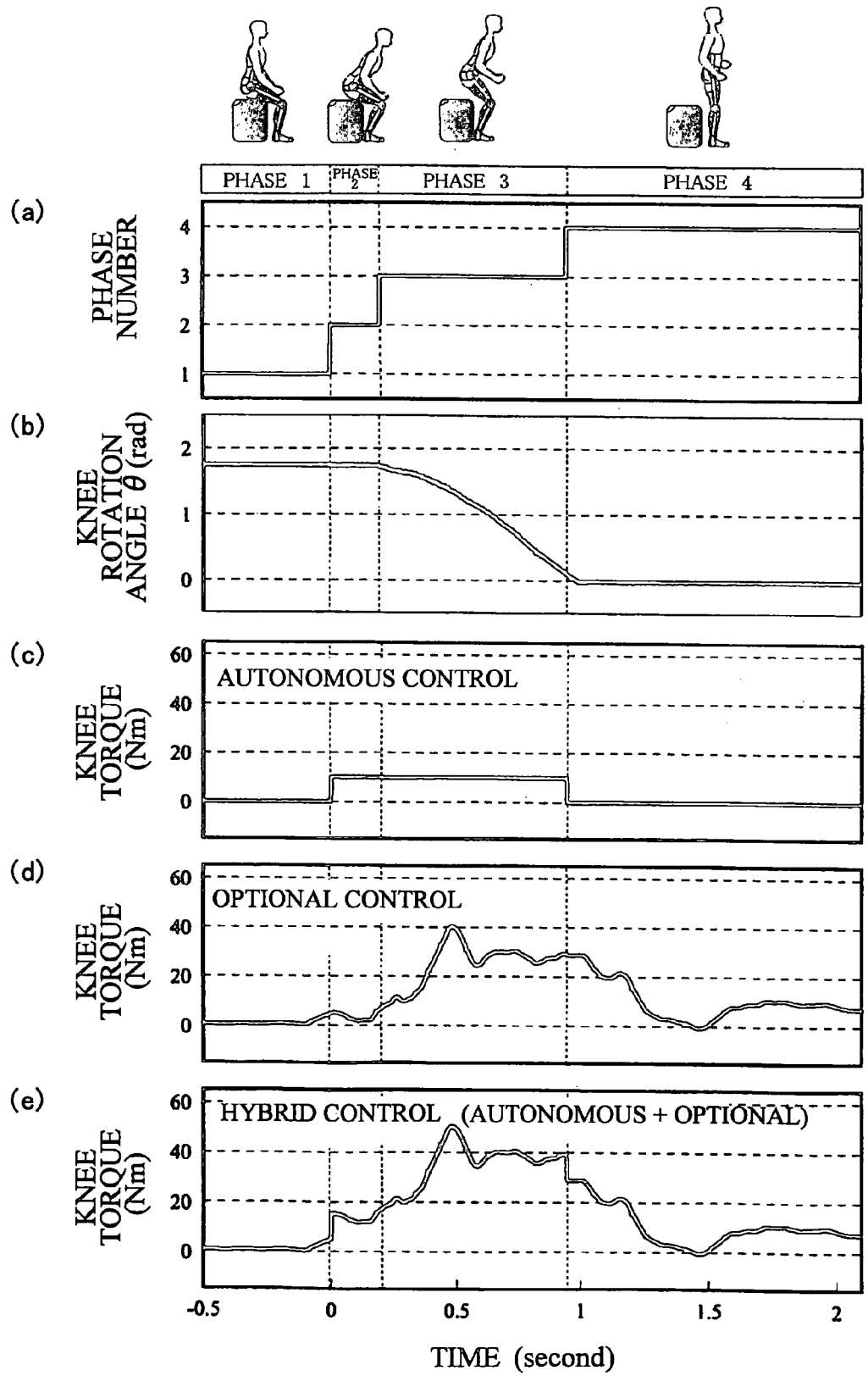
FIG. 21 is a diagram showing an experimental result of the change of the torque of the knee actuator obtained by using the control which combines the optional command signal and the autonomous command signal in the example 2.

This example is for explaining the effect of the second embodiment. FIG. 21 shows the experimental result of the rising action in which the wearer rises from the state in which he sat on the chair and the power application is carried out with the combination of autonomous control and optional control. FIG. 21 (c) shows the change of the torque of the knee actuator according to the command signal d1 by autonomous control. FIG. 21 (d) shows the change of the torque of the knee actuator according to the command signal d2 by optional control. FIG. 21 (e) shows the change of the torque of the knee actuator according to the total command signal d3 which is obtained by combining the command signal d1 by autonomous control and the command signal d2 by optional control. FIG. 21 (a) shows a phase number and FIG. 21 (b) shows the change of the knee rotation angle θ.

Figure 22:
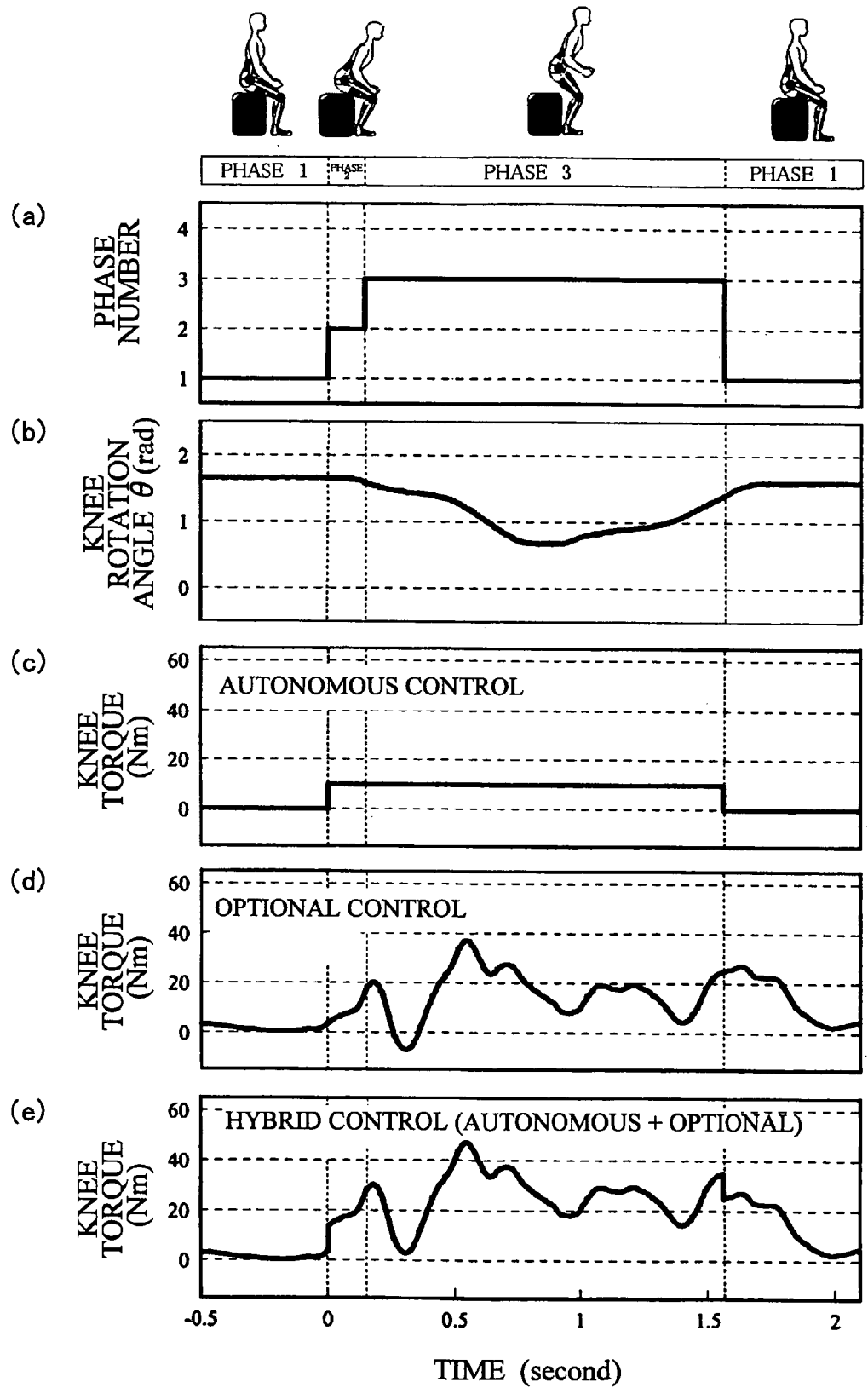
FIG. 22 is a diagram showing another experimental result of the change of the torque of the knee actuator obtained by using the control which combines the optional command signal and the autonomous command signal in the example 2.

FIG. 22 shows the experimental result of the rising action when the wearer rises from the state in which the wearer sat on the chair but he sits down after rising to the middle, and the power application is carried out with the combination of autonomous control and optional control. FIG. 22 (a) shows a phase number and FIG. 22 (b) shows the change of the knee rotation angle θ.

As is apparent from the graph of FIG. 22 (e), the torque of the actual knee actuator increased rapidly in the rising of phase 2, and fell rapidly in the falling of phase 3. Since the torque increased rapidly at the front edge of phase 2 corresponding to the rising from the chair, the knee actuator started rotation in accordance with the wearer's intention, and the wearer was able to perform the rising action comfortably while having a good feeling of power assistance.

In the falling of phase 3, the torque by autonomous control is promptly set to 0, and the situation which gives the wearer the torque which pushes out the wearer carelessly can be prevented, and the sense of incongruity given to the wearer can be suppressed.

As a result, in all the processes of phases 1-4, the wearer was able to have a good feeling of power assistance and was able to operate smoothly and comfortably.

On the other hand, when the torque according to command signal d by the optional control is used as shown in FIG. 21 (d), the rising is inadequate, the driving of the knee actuator cannot be started quickly in a comfortable manner. Since the torque according to the command signal d by the autonomous control shown in FIG. 21 (c) is a fixed torque which differs from the torque which changes in process, a series of comfortable and smooth actions cannot be performed.

That is, it is turned out that both the quick starting and the torque matched with the action of the wearer can be obtained only with the combination of the optional control and the autonomous control mentioned above.

On the other hand, as is apparent from the graph of FIG. 22 (e), when the wearer sits down immediately after rising, the torque increased rapidly at the front edge of phase 2 corresponding to the rising from the chair. The knee actuator started rotation in accordance with the wearer's intention, and the wearer was able to perform the rising action comfortably while having a good feeling of power assistance.

In the middle of phase 3, generation of the biosignal a is controlled, even if the torque by the optional control decreases and the torque by the autonomous control in the rising direction is added, the influence is cancelled by each other and the whole torque was not so large as to give the sense of incongruity in the action to sit on the chair. As a result, even if the wearer changes the action (task) suddenly, the wearer was able to have a good feeling of power assistance, and was able to perform the action smoothly and comfortably.

On the other hand, when the torque according to the command signal d by the optional control is used as shown in FIG. 22 (d), the rising is inadequate, and the driving of the knee actuator cannot be started quickly in a comfortable manner. When the torque according to the command signal d by the autonomous control is used as shown in FIG. 22 (c), changing suddenly from phase 3 to phase 1 caused the fixed torque to exert in the opposite direction of the action, and it was uncomfortable.

Thus, even when performing suddenly an action which is not a series of actions, the combination of the optional control and the autonomous control mentioned above is useful to prevent the sense of incongruity from being given to the wearer.

The present invention is not limited to the above-described embodiments and variations and modifications may be made without departing from the scope of the present invention.

The invention claimed is:

1. A wearable action-assist device which assists or executes an action of a wearer by substituting for the wearer, comprising:
   an action-assist tool including an actuator which gives power to the wearer;
   a biosignal sensor detecting a biosignal from the wearer;
   a biosignal processing unit acquiring, from the biosignal detected by the biosignal sensor, a nerve transfer signal for operating a muscular line skeletal system of the wearer, and a myoelectricity signal accompanied with a muscular line activity of the wearer;
   a control unit generating a command signal for causing the actuator to generate power according to an intention of the wearer, by using the nerve transfer signal and the myoelectricity signal which are acquired by the biosignal processing unit; and
   a driving current generating unit generating a current according to the nerve transfer signal and a current according to the myoelectricity signal, respectively, based on the command signal generated by the control unit, to supply the respective currents to the actuator,
   wherein the biosignal processing unit comprises:
   a unit which amplifies the biosignal;
   a first filter which extracts the nerve transfer signal from the biosignal; and
   a second filter which extracts the myoelectricity signal from the biosignal.

2. The wearable action-assist device according to claim 1 wherein the wearable action-assist device comprises a physical quantity sensor which detects a physical quantity related to the action of the wearer.

3. The wearable action-assist device according to claim 1 wherein the driving current generating unit supplies to the actuator a total current of a pulse current which is generated according to the nerve transfer signal and a current which is generated so as to be substantially proportional to the myoelectricity signal, and causes operation of the actuator to start by supplying the pulse current.

4. The wearable action-assist device according to claim 3 wherein the driving current generating unit generates, when starting the supply of current to the actuator, the pulse current or the total current such that the pulse current or the total current is larger than a lower limit of current that is capable of driving the actuator.

5. The wearable action-assist device according to claim 2 wherein the wearable action-assist device comprises a database in which a given correspondence relation between each of respective standard parameters of a series of minimum action units or phases which constitute a wearer's action pattern classified as a task, and a power application rate or power assist rate of the actuator is stored, and
   wherein the control unit estimates a phase of a task which the wearer intends to perform, by comparing the physical quantity detected by the physical quantity sensor with a standard parameter stored in the database, the control unit determining a power assist rate according to the estimated phase based on the correspondence relation, and generating a command signal for causing the actuator to generate a power according to the power assist rate.

6. The wearable action-assist device according to claim 1 wherein, when the wearer operates by reflexes, the driving current generating unit supplies a current for driving the actuator in an opposite direction of the operation concerned for a predetermined time, and, after the predetermined time, the driving current generating unit supplies a current for driving the actuator in a direction towards the operation.

7. A method of controlling a wearable action-assist device which assists or executes an action of a wearer by substituting for the wearer, using an action-assist tool including an actuator which gives power to the wearer which action-assist tool is attached to the wearer, the method comprising:
   detecting a biosignal from the wearer by a biosignal sensor of the wearable action-assist device;
   acquiring, from the detected biosignal, a nerve transfer signal for operating a muscular line skeletal system of the wearer and a myoelectricity signal accompanied with a muscular line activity of the wearer, by a biosignal processing unit of the wearable action-assist device;
   generating, by a control unit of the wearable action-assist device, a command signal for causing the actuator of the action-assist tool to generate power according to an intention of the wearer, by using the nerve transfer signal and the myoelectricity signal; and
   generating, by a driving current generating unit of the wearable action-assist device, a current according to the nerve transfer signal and a current according to the myoelectricity signal, respectively, based on the generated optional command signal, to supply the respective currents to the actuator,
   wherein the acquiring comprises:
   amplifying the biosignal by an amplifying unit of the biosignal processing unit;
   extracting the nerve transfer signal from the biosignal by a first filter of the biosignal processing unit; and
   extracting the myoelectricity signal from the biosignal by a second filter of the biosignal processing unit.

8. The method of controlling the wearable action-assist device according to claim 7 wherein a total current of a pulse current which is generated according to the nerve transfer signal and a current which is generated so as to be substantially proportional to the myoelectricity signal is supplied to the actuator, and operation of the actuator is caused to start by supplying the pulse current.

9. The method of controlling the wearable action-assist device according to claim 8 wherein, when starting the supply of current to the actuator, the pulse current or the total current is generated such that the pulse current or the total current is larger than a lower limit of current that is capable of driving the actuator.

10. The method of controlling the wearable action-assist device according to claim 7 wherein the method further comprises:
  detecting a physical quantity related to the action of the wearer;
  estimating a phase of a task which the wearer intends to perform, by comparing the physical quantity with each of respective standard parameters of a series of minimum action units or phases which constitute an action pattern of the wearer classified as a task;
  determining a power assist rate according to the estimated phase based on the correspondence relation; and generating a command signal for causing the actuator to generate a power according to the power assist rate.

11. The method of controlling the wearable action-assist device according to claim 7 wherein, when the wearer operates by reflexes, a current for driving the actuator in an opposite direction of the operation concerned for a predetermined time is supplied, and, after the predetermined time, a current for driving the actuator in a direction towards the operation is supplied.

12. A computer-readable recording medium storing a program thereon which, when executed by a computer, causes the computer to execute the method of controlling the wearable action-assist device according to claim 7.

* * * * *